US007037719B1

(12) United States Patent
Buck et al.

(10) Patent No.: US 7,037,719 B1
(45) Date of Patent: May 2, 2006

(54) ENRICHED CENTRAL NERVOUS SYSTEM STEM CELL AND PROGENITOR CELL POPULATIONS, AND METHODS FOR IDENTIFYING, ISOLATING AND ENRICHING FOR SUCH POPULATIONS

(75) Inventors: David W. Buck, Heathfield (GB);
Nobuko Uchida, Palo Alto, CA (US);
Irving Weissman, Redwood City, CA (US)

(73) Assignee: StemCells California, Inc., Palo Alto, CA (US)

( * ) Notice: Subject to any disclaimer, the term of this patent is extended or adjusted under 35 U.S.C. 154(b) by 0 days.

(21) Appl. No.: 09/890,469

(22) PCT Filed: Feb. 11, 2000

(86) PCT No.: PCT/US00/03592

§ 371 (c)(1),
(2), (4) Date: Nov. 3, 2001

(87) PCT Pub. No.: WO00/47762

PCT Pub. Date: Aug. 17, 2000

Related U.S. Application Data

(63) Continuation-in-part of application No. 09/422,844, filed on Oct. 21, 1999, now Pat. No. 6,468,794.

(60) Provisional application No. 60/119,725, filed on Feb. 12, 1999, provisional application No. 60/168,407, filed on Dec. 1, 1999.

(51) Int. Cl.
*C12N 5/08* (2006.01)

(52) U.S. Cl. ...................... 435/368; 435/343

(58) Field of Classification Search ............... 435/332, 435/368, 343, 335; 424/93.7, 140.1, 153.1
See application file for complete search history.

(56) References Cited

U.S. PATENT DOCUMENTS

| 5,750,376 A | 5/1998 | Weiss et al. |
| 5,753,506 A | 5/1998 | Johe |
| 5,843,633 A | 12/1998 | Yin et al. |
| 5,851,832 A | 12/1998 | Weiss et al. |
| 5,968,829 A | 10/1999 | Carpenter |

FOREIGN PATENT DOCUMENTS

| WO | WO 94/02593 | 2/1994 |
| WO | WO 00/12683 | 3/2000 |

OTHER PUBLICATIONS

Geysen et al., J. Molecular Recognition 1: 32-41 (1988).*
Arsenijevic et al., Experimental Neurology 170: 48-62 (2001).*
Corbeil et al., *AC133 Hematopoietic Stem Cell Antigen: Human Homologue of Mouse Kidney Prominin or Distinct Member of a Novel Protein Family?* 91 BLOOD 2625 (1998).
De Wynter et al., *Characteristics of MACS Isolated CD34+AC133+ Hematopoietic Progenitor Cells*, 2 MACS & MORE 8 (1998).
Miraglia et al., *AC133, A New Antigen for Human Hematopoietic Stem Cells. Is Prominin the Murine Homologue?* 2 MACS & MORE 6 (1998).
Miraglia et al., *A Novel Five-Transmembrane Hematopoietic Stem Cell Antigen: Isolation, Characterization, and Molecular Cloning*, 90 BLOOD 5013 (1997).
Miraglia et al., *A Response to AC133 Hematopoietic Stem Cell Antigen: Human Homologue of Mouse Kidney Prominin or Distinct Member of a Novel Protein Family?* 91 BLOOD 4390 (1998).
Yin et al., *AC133, A Novel Marker for Human Hematopoietic Stem and Progenitor Cells*, 90 BLOOD 5002 (1997).
Uchida et al. Society for Neuroscience Abstracts 25 (1-2): 1767 (1999).
Corbein et al., Journal of Cell Science, 112:1023-1033 (1999).
Weigmann et al. Proc. Natl. Acad. Sci. USA, 94(23):12425-12430 (1997).
CD133 Cell Isolation Kit, MACS, (Miltenyi Biotec, Auburn, CA) (downloaded Dec. 11, 2001).

* cited by examiner

Primary Examiner—Robert C. Hayes
(74) Attorney, Agent, or Firm—Mintz, Levin, Cohn, Ferris, Glovsky and Popeo, P.C.; Ivor R. Elrifi, Esq.; Christina K. Stock, Esq.

(57) ABSTRACT

Enriched neural stem and progenitor cell populations, and methods for identifying, isolating and enriching for neural stem cells using reagent that bind to cell surface markers, are provided.

21 Claims, 14 Drawing Sheets

In vivo studies: Transplantation into NOD SCID mouse

- Human neural cells can be transplanted into the lateral ventrical of neonatal immunodeficient mice

- Engraftment and migration of human neurosphere cells were detected between 4-8 weeks after injection using a human specific Thy-1 antibody

Migration of Human Neural Cells into Olfactory Bulb

Progeny of 5F3+ sorted neurosphere cells migrated through the RMS into Olfactory Bulb.

human nuclear antigen

5F3+ sorted neurosphere cells (p8), 7 months post transplant

A  Rostral migratory stream (RMS)   B  Olfactory bulb

Hippocampus

ENRICHED CENTRAL NERVOUS SYSTEM STEM CELL AND PROGENITOR CELL POPULATIONS, AND METHODS FOR IDENTIFYING, ISOLATING AND ENRICHING FOR SUCH POPULATIONS

CLAIM OF PRIORITY

This application is a 35 U.S.C. §371 entry of PCT/US00/03592 filed Feb. 11, 2000, which claims priority to U.S. provisional patent application 60/119,725, filed Feb. 12, 1999; and is a continuation-in-part of United States utility patent application Ser. No. 09/422,844, filed Oct. 21, 1999, now U.S. Pat. No. 6,468,794 which claims priority to U.S. provisional patent application 60/168,407, filed Dec. 1, 1999.

TECHNICAL FIELD

This invention relates generally to enriched neural stem cell and progenitor cell populations, and methods for identifying, isolating and enriching for neural stem and progenitor cells, particularly central nervous system neural stem cells and progenitor cells, and most particularly to enriched populations of neurosphere initiating cells (NS-IC).

BACKGROUND OF THE INVENTION

Stem cell populations constitute only a small percentage of the total number of cells, but are of immense interest because of their ability to repopulate the body. The longevity of stem cells and the dissemination of stem cell progeny are desirable characteristics. There is significant commercial interest in these methods because stem cells have a number of clinical uses. There is also medical interest in the use of stem cells as a vehicle for gene therapy.

Proteins and other cell surface markers found on stem cell and progenitor cell populations are useful in preparing reagents for the separation and isolation of these populations. Cell surface markers are also useful in the further characterization of these important cells.

Yin et al., U.S. Pat. No. 5,843,633, incorporated herein by reference, describes a monoclonal antibody called AC133, which binds to a surface marker glycoprotein on hematopoietic stem and progenitor cells. The AC133 antigen is a 5-transmembrane cell surface antigen with a molecular weight of 117 kDa. Expression of this antigen is highly tissue specific, and has been detected on a subset of hematopoietic progenitor cells derived from human bone marrow, fetal bone marrow and liver, cord blood, and adult peripheral blood. The subset of cells recognized by the AC133 antibody is $CD34^{bright}$, and contains substantially all of the CFU-GM activity present in the $CD34^+$ population, making AC133 useful as a reagent for isolating and characterizing human hematopoietic progenitor and stem cells.

However, surface markers specific to non-hematopoietic stem cells and progenitor cells, and particularly central nervous system neural stem cells and progenitor cells have not been identified. Further, the AC133 antibody has not been used in methods for identifying, isolating, or enriching for non-hematopoietic stem cells or progenitor cells, particularly central nervous system (CNS) neural stem cells and progenitor cells. There remains a need for tools, such as monoclonal antibodies that are useful in isolating and characterizing human non-hematopoietic progenitor and stem cells, and particularly central nervous system (CNS) neural stem cells and progenitor cells.

SUMMARY OF THE INVENTION

This invention provides methods for identifying, isolating, and enriching for human non-hematopoietic progenitor and stem cells, and particularly central nervous system (CNS) neural stem cells which can initiate neurospheres (NS-IC) and progenitor cells. The invention also provides for enriched populations containing CNS neural stem cells that can initiate neurospheres, and progenitor cells. A "neurosphere initiating cell (NS-IC)" is a cell that can initiate long-term neurosphere culture. A "neurosphere", in turn, is an aggregate or cluster of cells which includes neural stem cells and primitive progenitors. The identification, culture, growth, and use of neurospheres is disclosed in Weiss et al., U.S. Pat. No. 5,750,376 and Weiss et al., U.S. Pat. No. 5,851,832, both incorporated herein by reference. While the term "NS-IC" is defined by the ability or capacity of that cell to form a neurosphere, these cells may be appropriately grown in adherent culture (see, for example, Johe, U.S. Pat. No. 5,753,506, incorporated herein by reference), and it should be noted that the methods and populations described herein are not to be limited to suspension cultures of NS-IC. An NS-IC is nestin+ and has the capability to differentiate, under appropriate differentiating conditions, to neurons, astrocytes, and oligodendrocytes.

According to one embodiment of this invention, enriched populations of non-hematopoietic stem cells and progenitor cells, preferably CNS neural stem cells including NS-ICs, and progenitor cells, and method of identifying, isolating, or enriching for such cells, is achieved by contacting a population of cells containing at least one stem cell or NS-IC, or progenitor cell with a reagent that binds to surface marker glycoprotein antigen ("AC133 antigen") recognized by the AC133 antibody. In a preferred embodiment the reagent is the AC133 antibody (the AC133 antibody is alternately referred to herein as "5F3"). Use of traditional techniques for cell sorting, such as by immunoselection (e.g., FACS), then permits identification, isolation, and/or enrichment for cells in which contact between the reagent and the AC133 antigen has been detected.

In another embodiment, this invention provides a novel antibody, herein called 5E12, that may be used to provide enriched populations of non-hematopoietic stem cells and progenitor cells, preferably CNS neural stem cells that can initiate neurospheres and progenitor cells, and may be used in methods of identifying, isolating, or enriching for such cells, by contacting a population of cells containing at least one stem cell NS-IC, or progenitor cell with the 5E 12 antibody, which binds to a surface marker glycoprotein antigen other than the AC133 antigen.

In a preferred embodiment, the cells of this invention, preferably the CNS neural stem cells, are additionally characterized as lacking cell surface markers for CD45 and CD34.

In a further embodiment, this invention provides a novel antibody, herein called 8G1, believed to recognize CD24, which permits subselection between populations of CNS neural stem cells (characterized as $8G1^{-/lo}$) and populations of CNS progenitor cells (characterized as $8G1^+$).

BRIEF DESCRIPTION OF THE FIGURES

FIG. 9A is a flow cytometric separation of fresh fetal brain cells based on AC133 expression. Human fetal brain cells were enzymatically dissociated. Cells were stained with mAbs against CD34, CD45 and AC133, and separated into $AC133^-$ and $AC133^+$ fractions. The residual hematopoietic and endothelial cells were excluded by gating $CD45^-$ and $C34^-$, respectively. The sorted $AC133^-$ (FIG. 9B) and $AC133^+$ (FIG. 9C) subsets were cultured in the serum free media and the proliferation of these sorted cells were monitored for 15 days.

FIG. 10A is a quantitative analysis of NS-IC activity by limiting dilution analysis after cell sorting. Sorted cells were plated in a series of limiting cell doses into 96 well-plates by the FACS-ACDU. FIG. 10B shows the clonal expansion of neural stem/progenitor cells. Neurospheres can be derived from single sorted $AC133^+$ cell directly isolated from fetal brain or from a single $AC133^+$ cell from sorted/expanded cultured neurospheres. FIG. 10C shows the differentiation capacity of clonally derived neurosphere cells. Progeny of single cell-derived neurospheres can be differentiated into neurons (-tubulin, green) and astrocytes (GFAP, red).

FIG. 12A is a schematic diagram of adult mouse brain. Sites where human cell engraftment was evaluated are noted in the diagram. SVZ, subventricular zone; RMS, rostral migratory stream. FIG. 12B shows the detection of human neural cells in the SVZ. A sagittal section of the transplanted mouse brain was stained with anti-human nuclear antigen (FITC, green) and GFAP (Cy-5, blue). FIG. 12C shows the detection of proliferating human neural cells in the SVZ. The sagittal section of the transplanted mouse brain was stained with anti-human nuclear antigen (FITC, green), Ki67 (Cy-3, red) and GFAP (Cy-5, blue). Most of human nuclear antigen positive cells in the SVZ also co-expressed the proliferation marker, Ki67.

FIG. 13A shows the progeny of $AC133^+$ sorted/expanded neurosphere cells migrate through the RMS. In the RMS, the array of human nuclear antigen$^+$ cells, was also positive with Hoechst 33234 counter staining (pink) (i). The human nuclear antigen positive cells (Cy-3, red) in the RMS were co-localized with β-tubulin expression (Alexia 488, green) (ii). Some of these cells were clearly double positive (ii, arrow). In a different section, cells in the RMS were stained with human specific N-CAM (FITC, green) and GFAP (Cy-5, blue) (iii) FIG. 13B shows the migration and differentiation of human neural cells into the olfactory bulb. In the olfactory bulb, human nuclear antigen positive cells were distributed into the glomerular layer of the olfactory bulb (i and ii). In some cases, human N-CAM$^+$ neuronal cells were detected (iii).

FIG. 14A shows the detection of proliferating human neural cells in the subgranular zone of the dentate gyrus. The sagittal section of the transplanted mouse brain was stained with anti-human nuclei (FITC, green), Ki67(Cy-3, red) and GFAP (Cy-5, blue). Some human nuclear antigen$^+$ cells were co-stained with Ki 67 (arrow). FIG. 14B shows the detection of human neurons in the dentate gyrus. The sagittal section of the transplanted mouse brain was stained with anti-human nuclear antigen (Cy-3, red) and -tubulin (Alexia 488, green). One of two human nuclear antigen-positive cells was also positive for -tubulin (arrow).

DETAILED DESCRIPTION OF THE INVENTION

A population of cells exists within the adult central nervous system (CNS) which exhibit stem cell properties, in their ability to self-renew and to produce the differentiated mature cell phenotypes of the adult CNS. These stem cells are found throughout the CNS, and particularly in the subventricular regions, and dentate gyms of the hippocampus.

Growth factor-responsive stem cells can be isolated from many regions of the neuraxis and at different stages of development, of murine, rodent and human CNS tissue. These cells vary in their response to growth factors such as EGF, basic FGF (bFGF, FGF-2) and transforming growth factor alpha (TGF∝), and can be maintained and expanded in culture in an undifferentiated state for long periods of time. Both adult and embryonic murine progenitor cells respond to EGF and grow as spheres of undifferentiated cells. These cells show the characteristics of stem cells in that they are multipotent, and under serum containing conditions can differentiate into neurons, astrocytes and oligodendrocytes, as well as maintaining a subpopulation which remains undifferentiated and continues to proliferate under EGF administration. Murine EGF-responsive progenitor cells express mRNA for the EGF receptor in vitro. Human CNS neural stem cell cultures have also been identified. The identification, culture, growth, and use of mammalian, including human, neural stem cell cultures, either as suspension cultures or as adherent cultures, is disclosed in Weiss et al., U.S. Pat. No. 5,750,376 and Weiss et al., U.S. Pat. No. 5,851,832, both incorporated herein by reference. Similarly, Johe, U.S. Pat. No. 5,753,506, incorporated herein by reference, refers to adherent CNS neural stem cell cultures. When cultured in suspension, CNS neural stem cell cultures typically form neurospheres.

Figure 1:
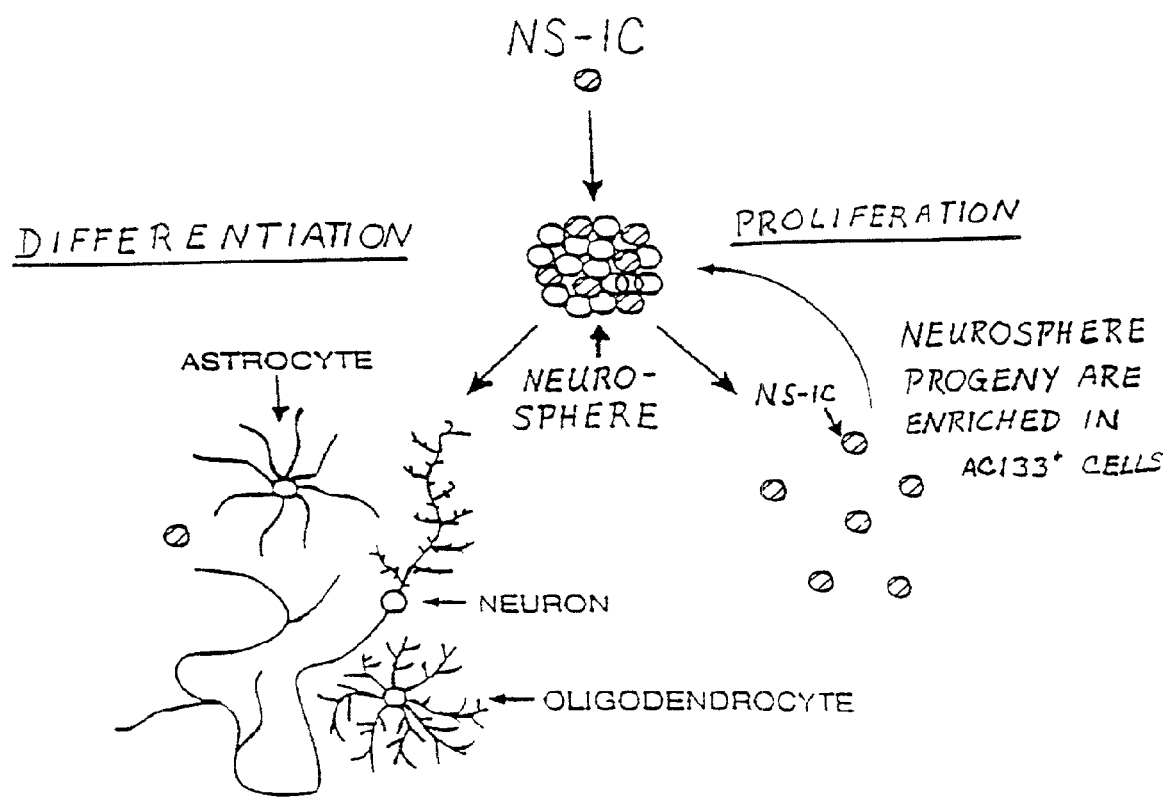
FIG. 1 is a diagram illustrating the proliferation and differentiation of a NS-IC.

FIG. 1 is shows the proliferation of a NS-IC as it develops into a neurosphere, and subsequent differentiation into neuronal and glial phenotypes, as well as generation of a progeny NS-IC. In the presence of one or more proliferation-inducing growth factors, the NS-IC divides and gives rise to a sphere of undifferentiated cells composed of more stem cells and progenitor cells (a "neurosphere"). When the clonally derived neurosphere is dissociated and plated as single cells, in the presence of one or more proliferation-inducing growth factors, each NS-IC can generate a new neurosphere. The cells of a single neurosphere are clonal in nature because they are the progeny of a single neural stem cell. In the continued presence of a proliferation-inducing growth factor such as EGF or the like, precursor cells within the neurosphere continue to divide resulting in an increase in the size of the neurosphere and the number of undifferentiated neural cells. The neurosphere is not immunoreactive for glial fibrillary acidic protein (GFAP; a marker for astrocytes), neurofilament (NF; a marker for neurons), neuron-specific enolase (NSE; a marker for neurons) or myelin basic protein (MBP; a marker for oligodendrocytes). However, cells within the neurosphere are immunoreactive for nestin, an intermediate filament protein found in many types of undifferentiated CNS cells (Lehndahl et al., 60 Cell 585–595 (1990), incorporated herein by reference). Antibodies are available to identify nestin, including the rat antibody referred to as Rat401. If the neurospheres are cultured in conditions that allow differentiation, the progenitor cells differentiate to neurons, astrocytes and oligodendrocytes. The mature phenotypes associated with the differentiated cell types that may be derived from the neural stem cell progeny are predominantly negative for the nestin phenotype.

The terminology used for undifferentiated, multipotent, self-renewing, neural cells has evolved such that these cells are now termed "neural stem cells." A neural stem cell is a clonogenic multipotent stem cell which is able to divide and, under appropriate conditions, has self-renewal capability for NS-IC and can include in its progeny daughter cells which can terminally differentiate into neurons, astrocytes, and oligodendrocytes. Hence, the neural stem cell is "multipotent" because stem cell progeny have multiple differentiation pathways. A neural stem cell is capable of self maintenance, meaning that with each cell division, one daughter cell will also be on average a stem cell.

The non-stem cell progeny of a neural stem cell are typically referred to as "progenitor" cells, which are capable of giving rise to various cell types within one or more lineages. The term "neural progenitor cell" refers to an undifferentiated cell derived from a neural stem cell, and is not itself a stem cell. Some progenitor cells can produce progeny that are capable of differentiating into more than one cell type. For example, an O-2A cell is a glial progenitor cell that gives rise to oligodendrocytes and type II astrocytes, and thus could be termed a "bipotential" progenitor cell. A distinguishing feature of a progenitor cell is that, unlike a stem cell, it does not exhibit self maintenance, and typically is thought to be committed to a particular path of differentiation and will, under appropriate conditions, eventually differentiate into glia or neurons.

The term "precursor cells" refers to the progeny of neural stem cells, and thus includes both progenitor cells and daughter neural stem cells.

Cell markers. This invention provides for the identification, isolation, enrichment, and culture of neural stem cells that are capable of forming neurospheres (NS-IC). NS-ICs are identified or selected through the binding of antigens, found on the surfaces of NS-ICs, to reagents that specifically bind the cell surface antigen.

One of these antigens is an antigen that binds to the AC133 monoclonal antibody. The AC133 antibody (herein referred to as the 5F3 antibody) is exemplary of antibody embodiments of reagents that recognize a human cell marker termed prominin. Prominin is a polytopic membrane protein expressed in various epithelial cells (Weigmann et al., 94(23) Proc. Natl. Acad. Sci. USA. 12425–30 (1997); Corbeil et al., 112 (Pt 7) J. Cell. Sci. 1023–33 (1999); Corbeil et al., 91(7) Blood 2625–6 (1998); Miriglia et al., 91(11) Blood 4390–1 (1998)). Various AC133 antibodies are described in U.S. Pat. No. 5,843,333, incorporated herein by reference. A deposit of the murine hybridoma cell line AC133 was made at the American Type Tissue Collection, 12301 Parklawn Drive, Rockville Md. 20852, on Apr. 24, 1997, and given the ATCC designation HB12346. These AC133 antibodies are capable of immunoselection for the subset of human cells of interest in this invention. Preferred AC133 monoclonal antibodies can be obtained commercially from Miltenyi Biotec Inc. (Auburn Calif.), including AC133/1-PE antibody (Cat #808-01) and AC133/2-PE antibody (Cat #809-01). For MACS separation, a 50:50 mixture of the monoclonal antibodies is preferred. The high tissue specificity of AC133 expression is particularly advantageous during enrichment for highly purified NS-IC populations.

5E12 is a novel monoclonal antibody generated against enzymatically-dissociated human fetal brain cells. The 5E12 monoclonal antibody was generated substantially according to the contralateral immunization method described in Yin, U.S. Pat. No. 5,843,633, incorporated herein by reference. The antigen to which 5E12 binds has a putative MW 125 kD, and is currently believed to be a distinct antigen from prominin.

CD45 is the T200/leucocyte common antigen. Antibodies to CD45 are commercially available. In a preferred embodiment, the cells of this invention and cultures containing them, are additionally characterized (in addition to being prominin positive) as lacking cell surface markers such as CD45.

CD34 is also known as gp105–120. Monoclonal antibodies to CD34 are commercially available, and CD34 monoclonal antibodies have been used to quantitate and purify lymphohematopoietic stem/progenitor cells for research and for clinical bone marrow transplantation.

The monoclonal antibody 8G1 is believed to recognize CD24 (antibodies to CD24 are commercially available), and specifically reacts with the 515 kilodalton -chain of human LRP/A2MR which is expressed in a restricted spectrum of cell types. A strong immunohistochemical reaction is seen in hepatocytes, tissue macrophages, subsets of neurons and astrocytes in the central nervous system, fibroblasts, smooth muscle cells, and monocyte-derived foam cells in atherosclerotic lesions in the arterial wall. The antibody can also be used for the characterization of a subset of myelomonocytic subtypes of chronic and acute leukemia (CD91). Antibodies to CD91 are commercially available.

Cell deposit. The 5E12.5 and 8G1.7 subject cultures are deposited under conditions that ensure that access to the cultures will be available during the pendency of the patent application disclosing them to one determined by the Commissioner of Patents and Trademarks to be entitled thereto under 37 C.F.R. § 1.14 and 35 U.S.C. § 122. The deposits are available as required by foreign patent laws in countries where counterparts of the subject application, or its progeny, are filed. However, the availability of a deposit does not constitute a license to practice the subject invention in derogation of patent rights granted by governmental action.

Further, the 5E12.5 and 8G1.7 subject culture deposits will be stored and made available to the public in accord with the provisions of the Budapest Treaty for the Deposit of Microorganisms, i.e., they will be stored with all the care necessary to keep them viable and uncontaminated for a period of at least 30 years after the date of deposit or for the enforceable life of any patent which may issue disclosing the cultures plus 5 years after the last request for a sample from the deposit. The depositor acknowledges the duty to replace the deposits should the depository be unable to furnish a sample when requested, due to the conditions of the deposits. All restrictions on availability to the public of the subject culture deposits will be irrevocably removed upon granting of a patent disclosing them.

Isolation, enrichment, and selection of cells. The population of cells from which NS-ICs are isolated can be a neural tissue, a population of cells is dissociated from neural tissue, or a population of cells in cell culture, e.g., a cells in a neurosphere culture or an adherent neural stem cell culture.

The invention provides for the isolation and identification of NS-ICs. Identification of a neurosphere initiating stem cell (NS-IC) involves contacting a population of neural cells (or which contains neural or neural derived cells) with a reagent that binds to AC133 antigen and detecting the contact between the reagent that binds to AC133 antigen and the AC133 antigen on the surface of cells. Those cells to which the reagent binds are identified as NS-ICs. The identity of those cells can be confirmed by assays to demonstrate that the cells are in fact NS-ICs, capable of neurosphere initiation, self renewal and multipotentcy.

The methods of this invention can also be used to isolate AC133$^+$ cells from AC133$^-$ cells using an AC133 antibody, by combining a population of neural cells which contains a fraction of NS-ICs with a reagent that specifically binds to the AC133 antigen, and then selecting for AC133$^+$ cells, to produce a selected population enriched in AC133$^+$ NS-ICs as compared with the population of neural cells before selection.

Accordingly, the invention further provides for the enrichment of NS-ICs from neural tissue or neural stem cell cultures (e.g., neurosphere suspension cultures or neural stem cell adherent cultures). The invention is thus useful for the enrichment of NS-IC from neural tissue in which stem cells and progenitor cells occur at low frequency, or may have been depleted, such as late embryo, juvenile, and adult tissue. One of skill in the art can combine a population of neural cells containing a fraction of NS-ICs with a reagent that specifically binds to the AC 133 antigen; and select for the AC133$^+$ cells. In this way, the selected AC133$^-$ cells are enriched in the fraction of NS-IC as compared with the population of neural cells.

The cell selection can be by any suitable means known in the art, including flow cytometry, such as by fluorescence activated cell sorting using a fluorochrome conjugated AC133 antibody. The selection can also be by high gradient magnetic selection using AC133 antibody is conjugated to magnetic particles. Any other suitable method including attachment to and disattachment from solid phase, is also contemplated within the scope of the invention.

One of skill in the art can derive the population of cells by immunoselection using an AC133 antibody. The population of cells should contain at least 30% AC133$^+$ NS-ICs, preferably at least 50–70% AC133$^+$ NS-ICs, and more preferably greater than 90% AC133$^+$ NS-ICs. Most preferable would be a substantially pure population of AC133$^+$ NS-ICs, comprising at least 95% AC133$^+$ NS-ICs. The degree of enrichment obtained, and actually used, depends on a number of factors, including the method of selection, the method of growth, and the cell dose of the cells that are placed in culture for the initiation of neurospheres.

The population of cells can be derived from late embryo, juvenile, or adult mammalian central nervous system (CNS) tissue, or it may be derived from existing cultures of neural stem cells, as described in Weiss, U.S. Pat. No. 5,750,376, or Johe, U.S. Pat. No. 5,753,506. In the most preferred embodiment, the NS-IC are human. In some embodiments, the AC133$^+$ cells in the population can be complexed to endothelial cells.

The in vitro cell cultures described herein containing an enriched population of AC133$^+$ NSICs are generally characterized in that the cultures stain positive for nestin and, in the presence of differentiation-inducing conditions, produce progeny cells that differentiate into neurons, astrocytes, and oligodendrocytes.

One of skill in the art can introduce an isolated AC133$^+$ cell to a culture medium, proliferate the isolated AC133$^+$ cell in culture; particularly as a neurosphere; culture the progeny of the isolated AC133$^+$ cell under conditions in which the isolated AC133$^+$ cell differentiates to neurons, astrocytes, and oligodendrocytes; then detect the presence of neurons, astrocytes, and oligodendrocytes. The presence of neurons, astrocytes, and oligodendrocytes characterizes the isolated AC133$^+$ cell as an NS-IC.

Typically AC133$^+$ NS-IC is cultured in a medium that permits the growth and proliferation of neurospheres. The culture in which the isolated AC133$^+$ cell proliferates can be a serum-free medium containing one or more predetermined growth factors effective for inducing multipotent neural stem cell proliferation. The culture medium can be supplemented with a growth factor selected from leukocyte inhibitory factor (LIF), epidermal growth factor (EGF), basic fibroblast growth factor (FGF-2; bFGF) or combinations thereof. The culture medium can be further supplemented with neural survival factor (NSF) (Clonetics, CA). The conditions in which the AC133$^+$ cell differentiates to neurons, astrocytes, and oligodendrocytes can be culturing the AC133$^+$ cell progeny on a laminin-coated surface in culture medium containing fetal bovine serum (FBS) without EGF, FGF-2 or LIF.

The invention also provides a method for identifying the presence of a growth factor that affects the growth of NS-IC. One of skill in the art combines a composition suspected of containing at least one growth factor that affects the growth of NS-IC with a composition comprising NS-IC, then determines the growth of the NS-IC as a function of the presence of the composition. Altered (increased, decreased, etc.) NS-IC growth indicates the presence in the composition of a growth factor that affects the growth of NS-IC. One can then further identify the growth factor.

Antibodies to AC133. Antibodies to AC133 may be obtained or prepared as discussed in U.S. Pat. No. 5,843,633, incorporated herein by reference. The AC133 antigen can be contacted with an antibody, such as various AC133 monoclonal antibodies, which have specificity for the AC133 antigen. An AC133 antibody is characterized by binding to the AC133 protein under Western blot conditions from reducing SDS-PAGE gels. The AC133 antigen has a molecular weight, based on commercially available standards, in the range of about 117 kDa. The AC133 antigen is expressed on a subset of progenitor cells derived from human bone marrow, fetal bone marrow and liver, cord blood, and adult peripheral blood.

Antibodies to AC133 antigen can be obtained by immunizing a xenogeneic immunocompetent mammalian host (including murine, rodentia, lagomorpha, ovine, porcine, bovine, etc.) with human progenitor cells. The choice of a particular host is primarily one of convenience. A suitable progenitor cell population for immunization can be obtained by isolating CD34$^+$ cells from cytokine mobilized peripheral blood, bone marrow, fetal liver, etc. A suitable progenitor cell population for immunization can be obtained from CNS neural stem cells or other NS-IC. Immunizations are performed in accordance with conventional techniques, where the cells may be injected subcutaneously, intramuscularly, intraperitoneally, intravascularly, etc. Normally, from about $10^6$ to $10^8$ cells will be used, which may be divided up into 1 or more injections, usually not more than about 8 injections, over a period of from about one to three weeks. The injections may be with or without adjuvant, e.g. complete or incomplete Freund's adjuvant, specol, alum, etc.

After completion of the immunization schedule, the antiserum may be harvested in accordance with conventional ways to provide polygonal antisera specific for the surface membrane proteins of progenitor cells, including the AC133 antigen. Lymphocytes are harvested from the appropriate lymphoid tisue, e.g. spleen, draining lymph node, etc., and fused with an appropriate fusion partner, usually a myeloma line, producing a hybridoma secreting a specific monoclonal antibody. Screening clones of hybridomas for the antigenic specificity of interest is performed in accordance with conventional methods.

AC 133 antibodies can be produced as a single chain, instead of the normal multimeric structure. Single chain antibodies are described in Jost et al., 269 J. Biol. Chem. 26267–73 (1994), incorporated herein by reference, and others. DNA sequences encoding the variable region of the heavy chain and the variable region of the light chain are ligated to a spacer encoding at least about 4 amino acids of small neutral amino acids, including glycine or serine. The protein encoded by this fusion allows assembly of a functional variable region that retains the specificity and affinity of the original antibody.

AC133 antibodies can be produced by use of Ig cDNA for construction of chimeric immunoglobulin genes (Liu et al., 84 Proc. Natl. Acad. Sci. 3439 (1987) and 139 J. Immunol. 3521 (1987), incorporated herein by reference. mRNA is isolated from a hybridoma or other cell producing the antibody and used to produce cDNA. The cDNA of interest may be amplified by the polymerase chain reaction using specific primers (U.S. Pat. Nos. 4,683,195 and 4,683,202). Alternatively, a library is made and screened to isolate the sequence of interest. The DNA sequence encoding the variable region of the antibody is then fused to human constant region sequences. The sequences of human constant regions genes may be found in Kabat et al., *Sequences of Proteins of Immunological Interest*. N.I.H. publication No. 91-3242 (1991). Human C region genes are readily available from known clones. The chimeric, humanized antibody is then expressed by conventional methods.

AC133 antibodies can be produced as antibody fragments, such as Fv, F(ab')$_2$ and Fab. Antibody fragments may be prepared by cleavage of the intact protein, e.g. by protease or chemical cleavage. Alternatively, a truncated gene is designed. For example, a chimeric gene encoding a portion of the F(ab')$_2$ fragment would include DNA sequences encoding the CH 1 domain and hinge region of the H chain, followed by a translational stop codon to yield the truncated molecule.

Immunostaining Biological samples are assayed for the presence of AC133$^+$ cells by any convenient immunoassay method for the presence of cells expressing the surface molecule bound by the subject antibodies. Assays may be performed on cell lysates, intact cells, frozen sections, etc. The antibodies available from Miltenyi Biotec Inc. (Auburn Calif.) are suitable for the direct immunofluorescent staining of cells.

Cell sorting. The use of cell surface antigens to NS-IC cells provides a means for the positive immunoselection of progenitor cell populations, as well as for the phenotypic analysis of progenitor cell populations using flow cytometry. Cells selected for expression of AC133 antigen may be further purified by selection for other stem cell and progenitor cell markers.

For the preparation of substantially pure progenitor and stem cells, a subset of progenitor cells is separated from other cells on the basis of AC133 binding. Progenitor and stem cells may be further separated by binding to other surface markers known in the art.

Procedures for separation may include magnetic separation, using antibody-coated magnetic beads, affinity chromatography and "panning" with antibody attached to a solid matrix, e.g. plate, or other convenient technique. Techniques providing accurate separation include fluorescence activated cell sorters, which can have varying degrees of sophistication, such as multiple color channels, low angle and obtuse light scattering detecting channels, impedance channels, etc. Dead cells may be eliminated by selection with dyes associated with dead cells (propidium iodide [PI], LDS). Any technique may be employed which is not unduly detrimental to the viability of the selected cells.

Conveniently, the antibodies are conjugated with labels to allow for ease of separation of the particular cell type, e.g. magnetic beads; biotin, which binds with high affinity to avidin or streptavidin; fluorochromes, which can be used with a fluorescence activated cell sorter; haptens; and the like. Multi-color analyses may be employed with the FACS or in a combination of immunomagnetic separation and flow cytometry. Multi-color analysis is of interest for the separation of cells based on multiple surface antigens, e.g. AC133$^+$ CD45$^-$, AC133$^-$ CD34$^+$, etc. Fluorochromes which find use in a multi-color analysis include phycobiliproteins, e.g. phycoerythrin and allophycocyanins; fluorescein and Texas red. A negative designation indicates that the level of staining is at or below the brightness of an isotype matched negative control. A dim designation indicates that the level of staining may be near the level of a negative stain, but may also be brighter than an isotype matched control.

In one embodiment, the AC133 antibody is directly or indirectly conjugated to a magnetic reagent, such as a superparamagnetic microparticle (microparticle). Direct conjugation to a magnetic particle is achieved by use of various chemical linking groups, as known in the art. Antibody can be coupled to the microparticles through side chain amino or sufhydryl groups and heterofunctional cross-linking reagents. A large number of heterofunctional compounds are available for linking to entities. A preferred linking group is 3-(2-pyridyidithio)propionic acid N-hydroxysuccinimide ester (SPDP) or 4-(N-maleimidomethyl)-cyclohexane-1-carboxylic acid N-hydroxysuccinimide ester (SMCC) with a reactive sulfhydryl group on the antibody and a reactive amino group on the magnetic particle.

Alternatively, AC133 antibody is indirectly coupled to the magnetic particles. The antibody is directly conjugated to a hapten, and hapten-specific, second stage antibodies are conjugated to the particles. Suitable haptens include digoxin, digoxigenin, FITC, dinitrophenyl, nitrophenyl, avidin, biotin, etc. Methods for conjugation of the hapten to a protein, i.e. are known in the art, and kits for such conjugations are commercially available.

To practice the method, the ACl 33 antibody is added to a cell sample. The amount of AC133 Ab necessary to bind a particular cell subset is empirically determined by performing a test separation and analysis. The cells and AC133 antibody are incubated for a period of time sufficient for complexes to form, usually at least about 5 min, more usually at least about 10 min, and usually not more than one hr, more usually not more than about 30 min.

The cells may additionally be incubated with antibodies or binding molecules specific for cell surface markers known to be present or absent on progenitor or stem cells.

The labeled cells are separated in accordance with the specific antibody preparation. Fluorochrome labeled antibodies are useful for FACS separation, magnetic particles for immunomagnetic selection, particularly high gradient magnetic selection (HGMS), etc. Exemplary magnetic separation devices are described in WO 90/07380, PCT/US96/00953, and EP 438,520. The AC133 Cell Isolation Kit (Miltenyi Biotec Inc., Auburn Calif.) can be used for the positive selection of AC133$^+$ cells. The kit provides a tool for single step isolation of AC133$^+$ cells. The AC133 Cell Isolation Kit contains FcR Blocking Reagent and MACS colloidal MicroBeads conjugated to the monoclonal mouse anti-human AC133 antibody.

The purified cell population may be collected in any appropriate medium. Various media are commercially available and may be used, including Dulbecco's Modified Eagle Medium (dMEM), Hank's Basic Salt Solution (HBSS), Dulbecco's phosphate buffered saline (dPBS), RPMI, Iscove's modified Dulbecco's medium (IMDM), phosphate buffered saline (PBS) with 5 mM EDTA, etc., frequently supplemented with fetal calf serum (FCS), bovine serum albumin (BSA), human serum albumin (HSA), etc.

Populations highly enriched for human progenitor or stem cells are achieved in this manner. The desired cells will be 30% or more of the cell composition, preferably 50% or more of the cell population, more preferably 90% or more of the cell population, and most preferably 95% or more (substantially pure) of the cell population.

Use of purified stem cell/progenitor cells. The AC133$^+$ stem cells/progenitor cells are useful in a variety of ways. The AC133$^+$ cells can be used to reconstitute a host whose cells have been lost through disease or injury. Genetic diseases associated with cells may be treated by genetic modification of autologous or allogeneic stem cells to correct a genetic defect or treat to protect against disease. Alternatively, normal allogeneic progenitor cells may be transplanted. Diseases other than those associated with cells may also be treated, where the disease is related to the lack of a particular secreted product such as hormone, enzyme, growth factor, or the like. CNS disorders encompass numerous afflictions such as neurodegenerative diseases (e.g. Alzheimer's and Parkinson's), acute brain injury (e.g. stroke, head injury, cerebral palsy) and a large number of CNS dysfunctions (e.g. depression, epilepsy, and schizophrenia). In recent years neurodegenerative disease has become an important concern due to the expanding elderly population which is at greatest risk for these disorders. These diseases, which include Alzheimer's Disease, Multiple Sclerosis (MS), Huntington's Disease, Amyotrophic Lateral Sclerosis, and Parkinson's Disease, have been linked to the degeneration of neural cells in particular locations of the CNS, leading to the inability of these cells or the brain region to carry out their intended function. By providing for maturation, proliferation and differentiation into one or more selected lineages through specific different growth factors the progenitor cells may be used as a source of committed cells. Neurospheres can also be used to produce a variety of blood cell types, including myeloid and lymphoid cells, as well as early hematopoietic cells (see, Bjornson et al., 283 Science 534 (1999), incorporated herein by reference).

The AC133$^+$ cells may also be used in the isolation and evaluation of factors associated with the differentiation and maturation of cells. Thus, the cells may be used in assays to determine the activity of media, such as conditioned media, evaluate fluids for growth factor activity, involvement with dedication of lineages, or the like.

The AC133$^+$ cells may be frozen at liquid nitrogen temperatures and stored for long periods of time, being thawed and capable of being reused. The cells will usually be stored in 5% DMSO and 95% fetal calf serum. Once thawed, the cells may be expanded by use of growth factors or stromal cells associated with stem cell proliferation and differentiation.

The following EXAMPLES are presented in order to more fully illustrate the preferred embodiments of the invention. These EXAMPLES should in no way be construed as limiting the scope of the invention, as defined by the appended claims.

EXAMPLE 1

AC133 Magnetic Cell Sorting (MACS)Positive Selected Fetal Brain Cells Contain Neurosphere Initiating Cell (NS-IC) Activity AC133$^+$ cells are prepared by the following method: Human fetal brain (FBR 10–20 gestational week ["g.w."]) were obtained from Advanced Bioscience Resources, INC (Oakland, Calif.) after obtaining informed consent. Human fetal brain tissues were cut into 1–3 mm cubed pieces using scalpels, transferred into 50 mL centrifuge tubes and wash once with 0.02% EDTA/PBS solution. Tissues were dissociated enzymatically in the presence of collagenase and hyaluronidase at 37° C. for 1 hr. Debris and aggregates were removed by filtering cell suspensions through 70 micron filter cup.

AC133$^+$ human fetal brain cells were separated by using paramagnetic antibody microbeads, AC133/1 Cell isolation Kit (Cat. # 508-01, Miltenyi Biotec, Auburn, Calif.). MACS separations were performed based on instruction accompanied with the kit. In a representative flow cytometric MACS separation from a typical AC133$^+$ isolation, about 44% of the cells were AC133$^+$ CD45$^-$, while about 2% were CD34$^+$ (These CD34$^-$ cells were endothelial cells complexed to the purified NS-IC).

The AC133+ selected cells which resulted from the method described above (using brain 18 g.w.) were still heterogeneous. The cells tended to form a complex with endothelial cells.

Endothelial cells were identified as CD34− or CD105−. AC133 MACS separation also enriches CD34− endothelial cells which are associated with AC133+ cells. (After passaging, the NS-IC separate from the complexed endothelial cells and purified NS-IC can be obtained.)

AC133+ MACS separated cells were cultured in the presence of media containing EGF, FGF-2, and LIF, as described above. In general, cells from early gestational age fetal brain (5–12 g.w.) were enriched for NS-IC and no enrichment was required to initiate neurosphere cultures. On the other hand, cells from older fetal brain samples (16–20 g.w.) contained far less NS-IC activity and required enrichment for initiating neurosphere cultures. In other words, AC133+ is useful for the enrichment of NS-IC from older gestational age humans brain tissue. AC133+ MACS separated cells from fetal brain (18 g.w.) were enriched for NS-IC activity, while whole human fetal brain cells (18 g.w.) without AC133+ MACS separation failed to initiate neurosphere cultures.

Neurosphere cells established from AC 133 MACS cells express nestin, as tested after ~7 days in culture and detected by rabbit anti-human nestin polyconal antibodies. For example, among the neurosphere cells available from CytoTherapeutics (Sunnyvale, Calif.), FBR 1069 (18 g.w.) and FBR 1070 (20 g.w.) expressed nestin. When induced to differentiate, the AC133+MACS-derived neurosphere cells could differentiate into neurons and astrocytes, as detected by P-tubulin staining for neurons and GFAP staining for astrocytes. In this particular differentiation assay, neurosphere cells were cultured onto a laminin-coated surface in the presence of 1% FBS and without EGF, FGF-2 and LIF.

Other differentiation assay can be used to induce differentiation of NS-IC to neurons, astrocytes and oligodendrocytes.

EXAMPLE 2

AC133 is a Critical Cell Surface Marker Expressed on Cells from Long-Term Neurosphere Culture A long-term neurosphere cell culture, 8.5 FBR, was obtained from CytoTherapeutics Inc. (Providence, R.I.). The 8.5 FBR neurosphere cells express AC133 relatively uniformly. These 8.5 FBR cells are also Thy-1+, CD166+, and HLA-DR+. When Ex Vivo 15 was used as basal media, higher percentage of neurosphere cultures initiated from primary brain tissue from 18 g.w. It is therefore possible to evaluate AC133+ fraction of cells in developing neurosphere cultures. The proportion of AC133+ cells increased as neurosphere developed. Once neurosphere cells were well established, virtually all cells forming neurospheres expressed AC133.

EXAMPLE 3

Neurosphere Initiating Cells can be Separated Using Monoclonal Antibody, AC133; Flow Cytometry Cell Sorting (FACS) Approach The purpose of this EXAMPLE is to test whether AC133+ cells were the only cells in the brain that have pluripotent NSC activity. mAb against human CD45 was used to exclude blood cell contamination in fetal tissue. In some cases, mAb against human CD34 was also used to exclude endothelial cells and endothelial-neural progenitor complexes. The fetal brain cells were thus defined as CD45− CD34−. To measure neural stem cells and primitive progenitor activities, a NS-IC assay was established to determine frequency of NS-IC in a given population. When NS-IC are rare and express AC133 antigen uniformly, NS-IC can be enriched by AC133+selection, and correspondingly depleted in other fractions.

Source of monoclonal antibodies. AC133 antigen was defined by two mAbs AC133/1 and AC133/2, both conjugated with phycoerythrin, which are available through Miltenyi Biotec (Auburn, Calif.). Anti human CD45−FITC and Glycophrin A-FITC were obtained from CALTAG (Burlingame, Calif.) and Coulter (Miami, Fla.) respectively. Anti-human allophycocyanin-conjugated CD34 was obtained from BDIS (San Jose, Calif.).

Cell preparation. FBR were dissociated by collagnease and hyaluronidase, and still contained endothelial-progenitor complex, which prevented the isolation of a candidate of NSC in single cell suspension (endothelial cells are CD45+). To dissociate this endothelial cell-NS-IC complex, FBR cells processed as described above, were further treated with trypsin for 10–15 min. The AC133 antigen, CD45 antigen and CD34 antigen were resistant for trypsin treatment, while Glycophrin A was sensitive.

After trypsin digestion, cells were washed and stained with mAbs against CD45, Glycophrin A, AC133 and CD34. No immunomagnetic bead selections were used. The cells were incubated for 20–60 min on ice. After the final wash, the cells were resuspended in HBSS solution containing 1 μg/mL propidium iodine (PI). The labeled cells were analyzed and sorted with a dual-laser FACS (Becton Dickinson, San Jose). Dead cells were excluded from analysis by their PI staining characteristics. After sorting purity of sorted cell populations were checked by FACS reanalysis. A representative FACS profiles of before sorting and post-sorting of AC133+ CD45− cells (NS-IC, 5% of the starting cells) and AC133− CD45− cells (~87% of the starting cells) was performed.

NS-IC activity is highly enriched in the AC133+ but not the AC133− subset. FBR cells (typically 16–20 g.w.) were typically sorted for CD45− CD34− AC133− and CD45− CD34− AC133+ fractions. No significant NS-IC activity resided in CD45+ or CD45−CD34+ populations in FBR.

The sorted cells were cultured in the neurosphere media described above. Typically, Ex Vivo 15 or combination of Ex Vivo 15, D-MEM, F-12 media were used as a basal medial. To maximize neurosphere development, the sorted cells were typically cultured in the presence of LIF, FGF-2, EGF and neural survival factor, NSF (Cat. CC-4323, Clonetics, San Diego, Calif.).

A single cell suspension was obtained after cell sorting. After 4–5 days in vitro culture, the AC133+ cells started to proliferate and small neurospheres were observed 8–10 days post culture initiations. The cells could initiate neurospheres when cultured in the presence of LIF, FGF-2, EGF without NSF. Neurosphere cultures were initiated from four out of four FBR tissues (18–20 g.w.) sorted for AC133+ CD45− or AC133+ CD45− CD34−.

In contrast, when AC133− CD45− FBR cells were placed in culture in the presence of LIF, FGF-2, and EGF, very few neurosphere formations were seen, and failed to passage to a new flask. When additional NSF was added in the growth media, some neurosphere initiation was observed. Thus, AC133− CD45− FBR cells were depleted in a significant amount of NS-IC.

EXAMPLE 4

AC133+ Cell Separation to Enrich for NS-IC Cells

AC133+ cell separation can effectively be used to enrich for NS-IC cells from tissue. Furthermore AC 133+ cell separation can further enrich for NS-IC cells from established preparations. In one test, AC133+ cell sorting of dissociated neurospheres (CytoTherapeutics, Providence, R.I.) provides a greatly enriched NS-IC culture and shows increased neurosphere establishment. Using that culture, the cell dose required to initiate a neurosphere in each well (i.e., 100% positive) can be reduced from 3,000–10,000 cells to about 30 cells (see, TABLE 1, below).

TABLE 1

| Tissue ID | Cell | Cell Dose | Score | # Well | % Positive | % Negative |
|---|---|---|---|---|---|---|
| FBR 1104 | Post trypsin | 1,000 | 6 | 24 | 25.0% | 75.0% |
| | Ex Vivo 15 | 3,000 | 20 | 24 | 83.3% | 16.7% |
| | LIF/EGF/FGF-2 | 10,000 | 24 | 24 | 100.0% | 0.0% |
| | | 30,000 | 12 | 12 | 100.0% | 0.0% |
| | | 100,000 | 12 | 12 | 100.0% | 0.0% |
| FBR 1104 | Post trypsin | 1,000 | 23 | 24 | 95.8% | 4.2% |
| | Ex Vivo 15 | 3,000 | 24 | 24 | 100.0% | 0.0% |
| | LIF/EGF/FGF-2/NSF | 10,000 | 24 | 24 | 100.0% | 0.0% |
| | | 30,000 | 12 | 12 | 100.0% | 0.0% |
| | | 100,000 | 12 | 12 | 100.0% | 0.0% |
| FBR 1104 | AC133 neg. selected cells | 1,000 | 0 | 24 | 0.0% | 100.0% |
| | Ex Vivo 15 | 3,000 | 1 | 24 | 4.2% | 95.8% |
| | LIF/EGF/FGF-2/NSF | 10,000 | 28 | 48 | 58.3% | 41.7% |
| | AC133+ selected cells | 10 | 2 | 24 | 8.3% | 91.7% |
| | Ex Vivo 15 | 100 | 24 | 24 | 100.0% | 0.0% |
| | LIF/EGF/FGF-2/NSF | 300 | 24 | 24 | 100.0% | 0.0% |
| | | 1,000 | 24 | 24 | 100.0% | 0.0% |
| FBR 1101 | Post trypsin | 1,000 | 9 | 24 | 37.5% | 62.5% |
| | Ex Vivo 15 | 3,000 | 16 | 24 | 66.7% | 33.3% |
| | LIF/EGF/FGF-2 | 10,000 | 23 | 24 | 95.8% | 4.2% |
| | | 30,000 | 12 | 12 | 100.0% | 0.0% |
| | | 100,000 | 12 | 12 | 100.0% | 0.0% |
| FBR 1101 | Post trypsin | 1,000 | 16 | 24 | 66.7% | 33.3% |
| | Ex Vivo 15 | 3,000 | 21 | 24 | 87.5% | 12.5% |
| | LIF/EGF/FGF-2/NSF | 10,000 | 24 | 24 | 100.0% | 0.0% |
| | | 30,000 | 12 | 12 | 100.0% | 0.0% |
| | | 100,000 | 12 | 12 | 100.0% | 0.0% |
| FBR 1101 | AC133+ selected cells | 1 | 9 | 96 | 9.4% | 90.6% |
| | Ex Vivo 15 | 10 | 42 | 60 | 70.0% | 30.0% |
| | LIF/EGF/FGF-2/NSF | 30 | 23 | 24 | 95.8% | 4.2% |
| | | 100 | 11 | 12 | 91.7% | 8.3% |

As shown in TABLE 1, the non-enriched fresh brain tissue ("FBR") used here (g.w. 20) may contain NS-IC in such numbers that it requires a cell dose of between 3,000 and 10,000 cells to initiate neurospheres in every well. By using the method of the invention, enriched populations can be obtained, such that a cell dose of 1,000 cells or less is required, and more preferably an enriched population such that a cell dose of less than 100 cells is required. As shown in TABLE 1, enrichment here has been achieved so that a cell dose of only about 30 cells is required per well to establish a neurosphere culture in each well. TABLE 1 also shows that when populations are depleted in AC133+ cells (FBR 1104 AC133 neg. selected cells), establishment of neurosphere cultures from those populations is markedly reduced.

Quantitative NS-IC assay. To assay for the presence of NS-IC, cell populations suspected of containing the multipotent NS-IC are subjected to clonal development. Cells are grown in proliferation medium to form neurospheres, then induced to differentiate to form neurons, astrocytes, and oligodendrocytes. The presence of neurons, astrocytes, and oligodendrocytes can be shown by immunostaining. For example, neurons stain for the presence of β-tubulin; astrocytes stain for the presence of GFAP; and oligodendrocytes stain for the presence of 04.

The quantitative NS-IC assay can be performed on unpurified tissue cells, on AC133+sorted cells, and on clonal neurosphere cell lines.

EXAMPLE 5

Cell Culture Media for Growth and Passage of NS-IC

Weiss et al., U.S. Pat. No. 5,750,376 and Weiss et al., U.S. Pat. No. 5,851,832 disclose "culture medium containing one or more predetermined growth factors effective for inducing multipotent neural stem cell proliferation" and "differentiation-inducing conditions" However, different basal media can be used, including, but not limited to:

D-MEM/F12 (Gibco BRL, Gaithersburg, Md.);
Ex Vivo 15 (Bio Whittaker, Walkersville, Md.);
Neural progenitor basal media, (Clonetics. San Diego, Calif.); or
combination of the basal media listed above.

A typical media formulation to culture human neurosphere cells is provided in TABLE 2.

TABLE 2

SERUM-FREE N2/EGF SUPPLEMENTED CULTURE MEDIUM FOR NEUROSPHERES

| Quantity | Reagents |
|---|---|
| 87 ml | DMEM/F12 (Gibco lot. 1012915; Cat. No. 11330-032) |
| 1 ml | N-2 Supplement (Gibco lot 1017018; Cat. No. 17502-014) |
| 1 ml | 0.2 mg/ml heparin (Sigma lot 28H0320; Cat. No. H-3149) |
| 1 ml | 0.2 M Glutamine (JCR lot 7N2320; Cat. No. 59202-77p) |
| 10 ml | 3% Glucose (Sigma, lot 37H0841; Cat. No. G-7021) |
| 20 μl | 100 μg/ml EGF (R&D lot CE107091; Cat. No. 236-EG) |
| 100 μl | 20 μg/ml FGF-2 (Gibco lot KCQ411; Cat. No. 13256-029) |
| 100 μl | 10 μg/ml LIF (R&D lot OX038021; Cat. No. 250-L) |

EGF is added to 100 ml base medium for human neurospheres after filtering the medium. EGF is relatively stable in the medium. FGF-2 and LIF are added when medium is ready to use. The final concentrations of the supplement reagents are:

| | |
|---|---|
| 5 g/ml | Insulin |
| 100 g/ml | Human transferrin |
| 6.3 ng/ml | Progesterone |
| 16.1 g/ml | Putrascine |
| 5.2 ng/ml | Selenite |
| 20 ng/ml | EGF |
| 20 ng/ml | FGF-2 |
| 10 ng/ml | LIF |

-continued

| 2 g/ml | heparin |
| 2 mM | L-glumtamine |
| 6 mg/ml | Glucose |

The optimization of media formulation permits a higher percentage of neurospheres initiated from primary brain tissue to be established. We prefer Ex Vivo 15 media. The optimization of media formulation also permits a more consistent growth of neuro spheres. To maximize neurosphere development, the NS-IC are typically cultured in the presence of LIF, bFGF, EGF and neural survival factor, NSF (Cat. CC-432', Clonetics, San Diego, Calif.). In one test, both trypsinized FBR 1101 neural cells and trypsinized FBR 1104 neural cells (CytoTherapeutics, Sunnyvale, Calif.), show increased growth when cultured in Ex Vivo 15 medium with LIF, bFGF, EGF, and NSF.

EXAMPLE 6

Direct Isolation of Human Neural Stem Cells from Fetal Brain by Cell Sorting

A large source of highly defined engraftable human cells capable of extensive neuronal regeneration could be an effective therapeutic product for the treatment of neurodegenerative disorders. To define reproducible methods for the enrichment of human neural stem cells (NSCs), we have developed and used monoclonal antibodies (mAbs) directed toward surface markers on human neural cells to identify and purify NSCs by fluorescence activated cell sorting (FACS). Based on FACS and immunohistochemical analyses, two mAbs, 5F3 and 5E12 were identified. They defined small subsets of fetal brain cells and displayed specific reactivity to cells in the floor plate and ependymal layer of the spinal cord (12 g.w), sites known to contain CNS stem cells. These mAbs, stain less than 5% of FBR cells, and greater than 95% of cells from long-term neurosphere cultures were positive.

As an example, two cell populations $5F3^+CD34^-CD45^-$ ($5F3^-$) and $5F3^-CD34^-CD45^-$ ($5F3^-$) were sorted and tested for their ability to initiate neurosphere cultures. The 5F3+ subset was highly enriched for neurosphere-initiating cell activity; they proliferated to form small neurosphere by 8–10 days in culture. In contrast, the sorted $5F3^-$ cells remained as a single cell suspension, failed to initiate neurospheres, and eventually died. The expanded $5F3^+$ sorted neurosphere cells were positive for nestin expression, and differentiated into neurons and glia following exposure to differentiation conditions. Using the NOD SCID mouse, in vivo studies show that at 8 weeks post transplantation the 5F3+neurosphere cells can engraft and migrate. These studies show that we have identified and enriched human NSCs based on cell surface markers and flow cytometry and demonstrated their activity using in vitro and in vivo assays.

Figure 5:
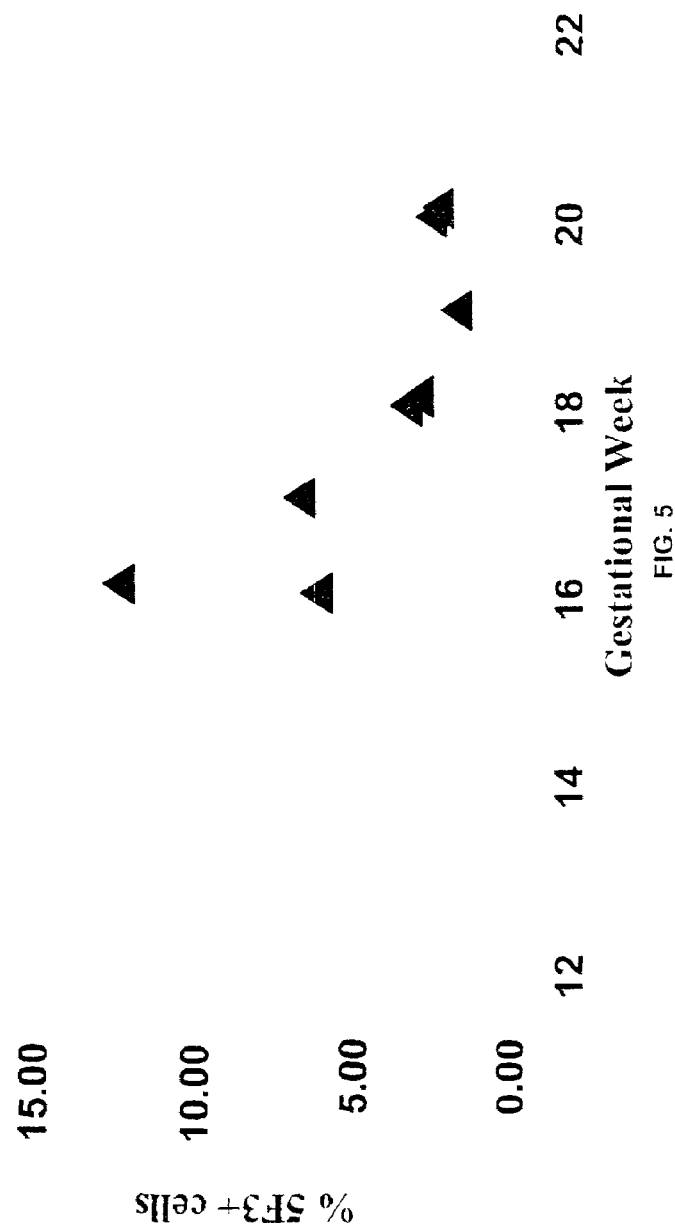
FIG. 5 is a chart showing the distribution of $5F3^+$ cells in fetal brain as a function of gestational age.

In further tests, we examined brain and spinal cord tissues over various gestational ages. The earlier (5–12 wk gestation) gestational ages have a higher frequency of neurosphere initiating cell (NS-IC) than later gestational ages (16–20 wk gestation). See, e.g., FIG. 5. Direct culturing of cells derived from these tissues leads to neurosphere initiation.

Our data (shown in the TABLE 3 below) demonstrate that cell population of neural cells enriched for $5F3^+$ cells are enriched for NS-IC activity, as much as 23 fold.

TABLE 3

| Population | % in brain | NS-IC | Range |
|---|---|---|---|
| Post processed brain cells (n = 8) | 100 | 1/819 | 1/304–1435 |
| 5F3⁻ sorted (n = 6) | 95 | 1/5434 | 1/4224–7772 |
| 5F3⁺ sorted (n = 6) | 4.6 | 1/36 | 1/10–74 |

Figure 2:
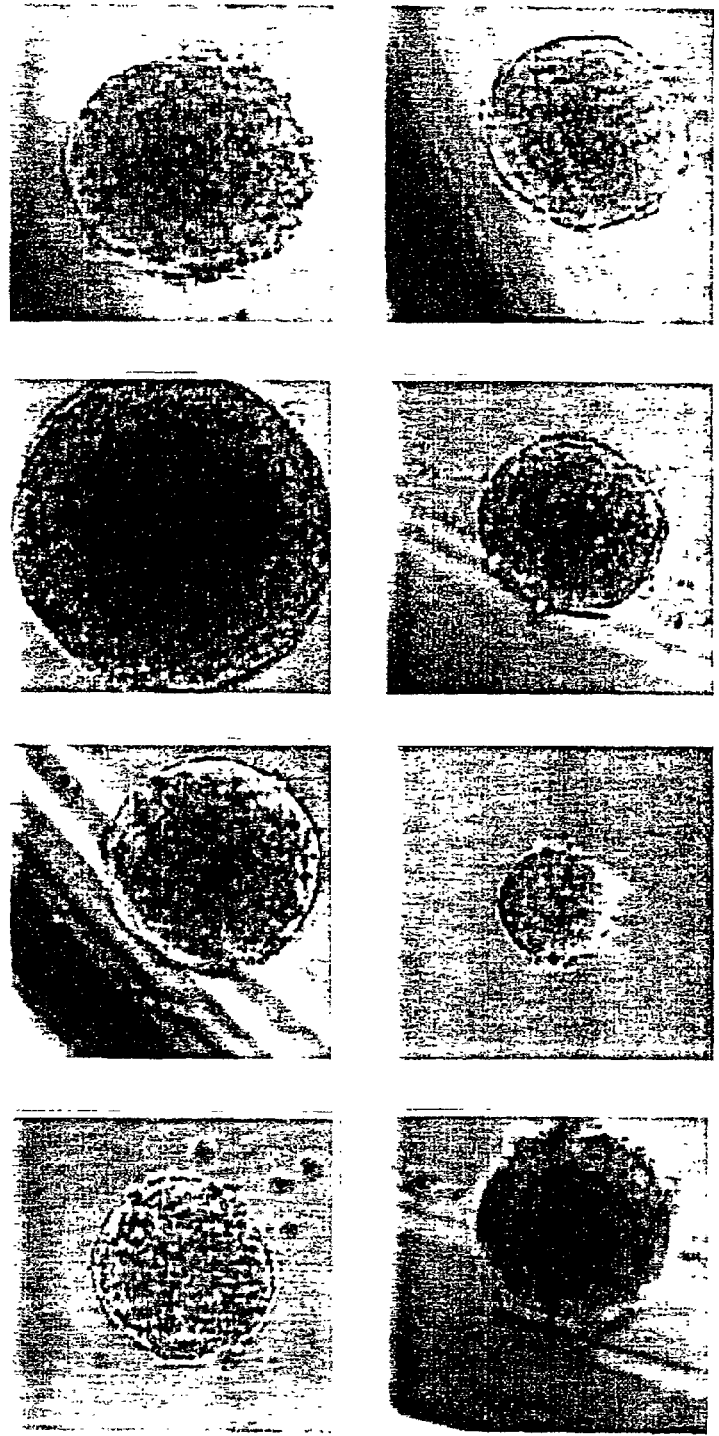
FIG. 2 is a series of photographs showing that neurosphere cultures can be initiated from single-cell sorted $5F3^+$ cells.

Further, as FIG. 2 shows, neurospheres can be derived from single-cell sorted $5F3^+$ cells. We have also demonstrated that self-renewal of neurosphere cells derived from $5F3^+$ sorted cells can be achieved by re-initiation of neurospheres from single cells (data not shown). Conversely, our data indicates that cell populations depleted of $5F3^+$ cells are also depleted for NS-IC activity.

EXAMPLE 7

Isolation of NS-IC by Different Markers

Figure 3:
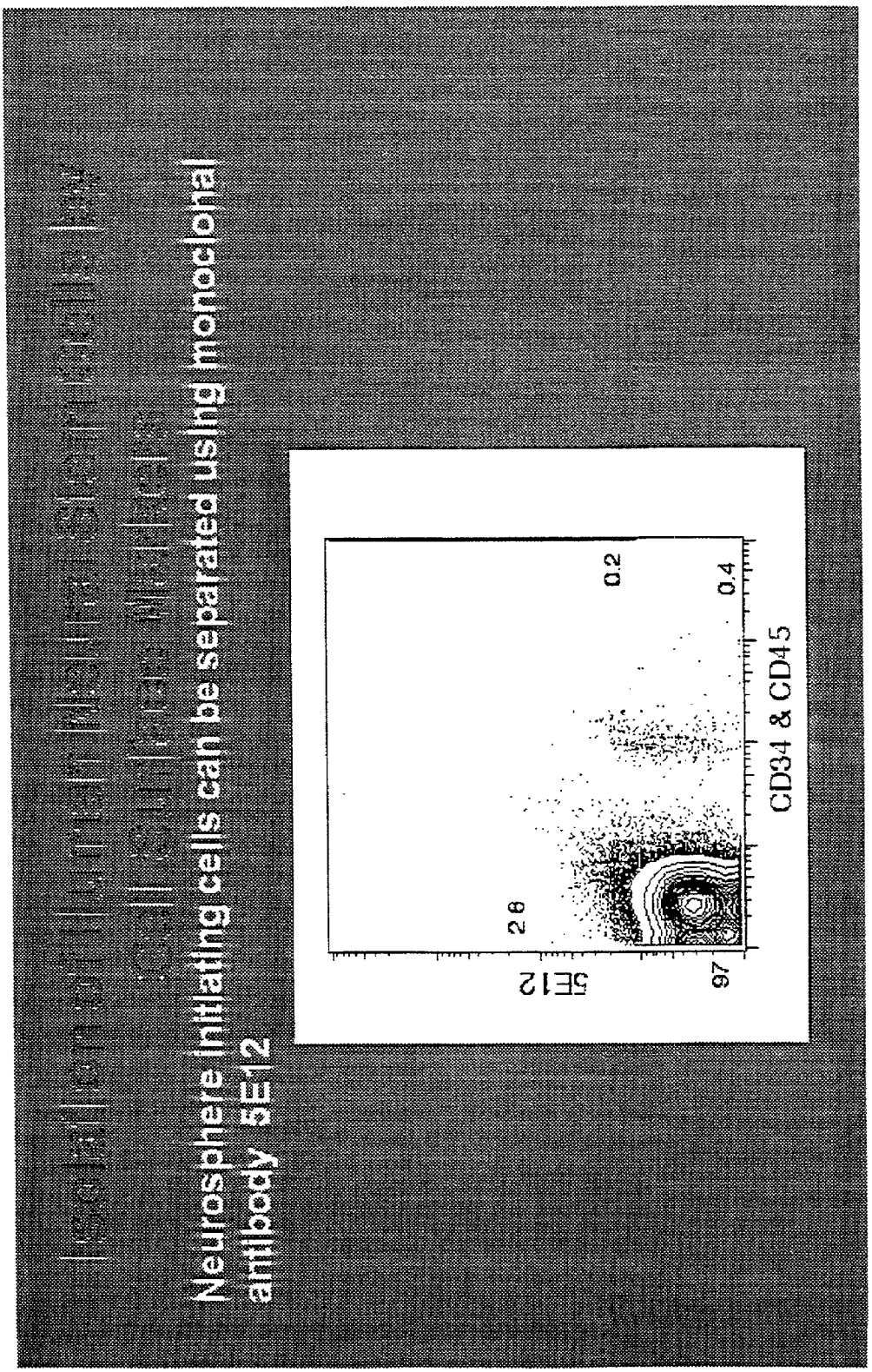
FIG. 3 is a dot plot of fluorescence activated cell sorting (FACS) data showing the isolation of human CNS neural stem cells using cell surface markers using the monoclonal antibody 5E12. The x axis represents cell staining for antibodies to CD34 and CD45. The y axis represents cell staining with the 5E 12 antibody.

As a second example, we sorted cell populations using a novel monoclonal antibody, 5E 12, described herein. The $5E12^+$ subset was enriched for neurosphere-initiating cell activity, as shown in TABLE 4 below. See also FIG. 3. Our data suggests that the antigen to the 5E12 antibody is co-expressed with the AC133 antigen on $5F3^-$ cells.

We also evaluated the 8G1 monoclonal antibody as a subselector for neural stem cells, as shown in TABLE 4 below. Cells that were $5F3^+$ and $8G1^{-/lo}$ displayed more stem cell-like properties, while cells that were $5F3^-$ and $8G1^{med/hi}$ displayed more progenitor cell-like properties.

TABLE 4

ENRICHMENT OF NS-IC BY 5F3, 5E12 AND 8G1 ANTIBODIES

| Population | % in brain | NS-IC | Range |
|---|---|---|---|
| Brain cells control (n = 8) | 100 | 1/819 | 1/304–1435 |
| 5F3– sorted (n = 6) | 95 | 1/5434 | 1/4224–7772 |
| 5F3+ (n = 6) | 4.6 | 1/36 | 1/10–74 |
| 5E12– (n = 2) | 97 | 1/1335 | 1/1259, 1411 |
| 5E12+ (n = 3) | 2.5 | 1/286 | 1/79–392 |
| 5F3+ 8G1$^{-/lo}$ (n = 3) | 1.1 | 1/23 | 1/15–34 |
| 5F3+ 8G1$^{mid/hi}$ (n = 3) | 1.7 | 1/63 | 1/38–105 |

*All sorted populations were CD34⁻ CD45⁻

EXAMPLE 9

In Vivo Studies NS-IC

Figure 6:
FIG. 6 is a series of photographs showing results of the transplantation of human neural cells into NOD SCID mouse.
Figure 7:
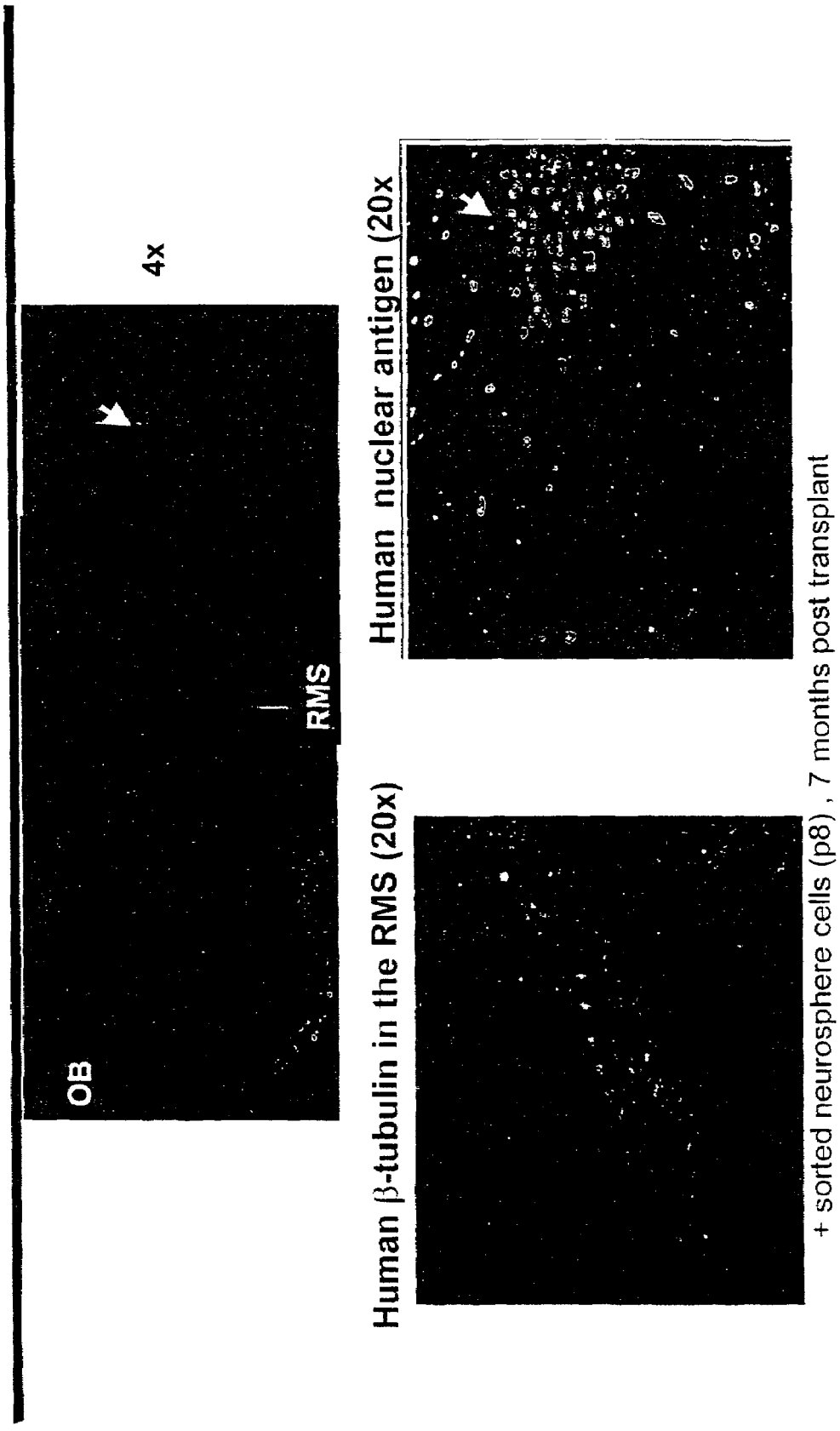
FIG. 7 is a series of photographs showing that the progeny of $5F3^+$ sorted cells migrate through the rostral migratory stream (RMS) when transplanted into a rodent model.
Figure 8:
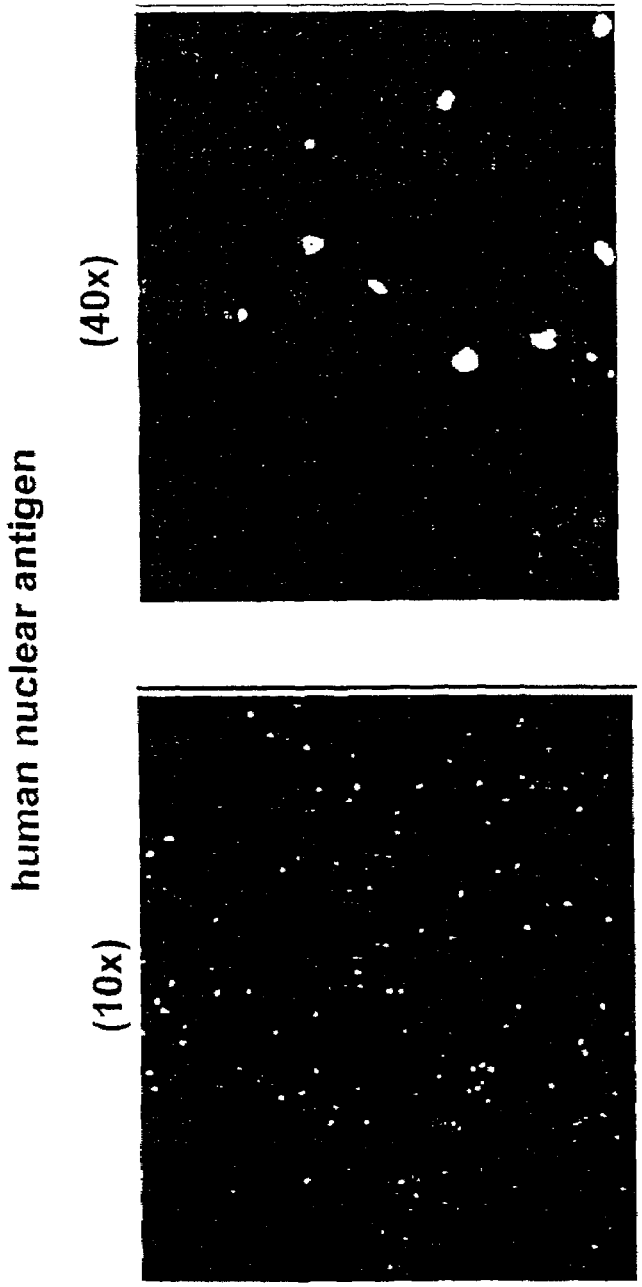
FIG. 8 is a series of photographs showing that the progeny of $5F3^+$ sorted cells migrate through the (RMS) into the olfactory bulb when transplanted into a rodent model.

We transplanted $5F3^+$-sorted NS-ICs (obtained as described above) into the lateral ventricles of neonatal immunodeficient mice, using conventional techniques. Engraftment and migration of human neurosphere cells were detected between 4–8 weeks after injection using a human specific Thy-1 antibody (see FIG. 6). As shown in FIG. 7, staining with human β-tubulin (a neuronal marker) and human nuclear antigen (for localization of human cells) revealed migration of the human neurosphere cells through the rostral migratory stream (RMS). Further, as shown in FIG. 8, localization using human nuclear antigen demonstrated that human neurosphere cells had migrated through the RMS to the olfactory bulb.

EXAMPLE 10

Direct Isolation of and Transplantation of Human Central Nervous System Stem Cells Introduction and summary. Stem cells, clonogenic cells with self-renewal and multilineage differentiation properties, have the potential to replace or repair damaged tissue. In this EXAMPLE, we have isolated clonogenic human brain stem cells (CNS-SC) that initiate neurosphere cultures and show both self-renewal and differentiation to neurons and glia. These non-genetically modified human CNS-SC are marked by monoclonal antibodies for surface markers. The cells are 5F3 (AC133)$^+$, 5E12$^+$, CD34$^-$CD45$^{-1\ and}$ $_{CD}$24$^{-/lo}$. Single AC133$^+$CD34$^-$CD45$^-$ sorted cells initiated neurosphere cultures and displayed multilineage differentiation. Once transplanted into brains of immunodeficient neonatal mice the sorted and expanded CNS-SC show potent engraftment, proliferation, migration and differentiation in a site-specific manner.

In this EXAMPLE, we show that mAbs 5F3 and the novel mAb, 5E12, detect a distinct subset of human fetal brain (FBr) cells. Fluorescence-activated cell sorting using these mAbs in conjunction with mAbs that mark contaminating blood and endothelial cells (CD34 and CD45) results in a subset of human FBr cells, AC133$^+$ CD34$^-$CD45$^-$. After cell sorting, the sorted cells are capable at the single cell level of neurosphere initiation, self-renewal, and multilineage differentiation, cells that we propose as human CNS-SC. These candidate human CNS-SC self-renewed and significantly expanded in neurosphere cultures, and differentiated in vitro to neurons and glia. The sorted and expanded candidate CNS-SC can be transplanted into the lateral ventricles of newborn NOD-SCID mouse brains, where they undergo apparently appropriate site-specific engraftment, continued self-renewal, migration and differentiation for at least 7 months.

Searching for CNS neural stem cell markers; Strategy. We hypothesized that candidate CNS-SC markers should be expressed on only a minor subset of FBr cells. Since there was evidence that the neurosphere cultures contain an enriched population of stem/progenitor cells, we hypothesized that the candidate neural stem cell markers should be more abundantly expressed on these cells. Thus, we screened through the mAbs used previously to define human hematopoietic stem cells (HSC).

Sorted populations were tested to determine whether they were enriched for neurosphere-initiating cells (NS-IC). Any mAb that cleanly separated FBr into 2 fractions (one fraction that established a neurosphere culture and one that did not) was considered a candidate mAb to help identify NS-IC. In the initial screen, mAbs were sought that positively stained a small fraction of FBr and a large fraction of long-term cultured neurosphere cells, and other mAbs (for negative selection) that stained most FBr cells but a small fraction of neurosphere cells. Enzyme dissociated FBr and long-term cultured neurosphere cells were stained with over 50 known mAbs.

A long-term neurosphere culture, 8.5 FBr has been described previously (Carpenter et al., 158 Exp. Neurol. 265–78 (1999)). These cells were cultured in standard human neurosphere media: D-MEM/F12 basal media with N-2 supplement (Gibco), 3% glucose, 0.2M glutamine and 0.2 mg/ml heparin in the presence of FGF-2 (20 ng/mL), EGF (20 ng/mL), and LIF (10 ng/mL). The cultured cells were harvested and dissociated enzymatically in the presence of collagenase for 5–10 min for passage or trypsinized to obtain single cell suspension for mAbs staining.

The neurosphere cells did not express the vascular and hematopoietic markers CD34 or CD45. In contrast, Thy-1, a critical cell surface marker that identified both mouse and human HSC, was expressed at high levels on virtually all FBr cells and neurosphere cells, and was therefore not useful. Interestingly, initial antibody screening revealed that another HSC marker, AC133, was expressed on only 1–5% of FBr cells derived from 16–20 gestational week (g.w.) tissue and on ~90% of cultured neurosphere cells.

Monoclonal antibody AC133 enriches for human CNS-SC. Human FBr tissue was obtained from the remains of the 16–20 gestation weeks (g.w.) fetuses from Advanced Bioscience Resources, Inc., according to NIH guidelines. FBr tissues were cut into 1–3 mm pieces using scalpels, transferred into 50 mL centrifuge tubes and washed once with 0.02% EDTA/PBS solution. Tissues were dissociated enzymatically in the presence of 0.1% collagenase (Roche, Indianapolis, Ind.) and 0.1% hyaluronidase (Sigma, St Louis, Mo.) at 37 degrees in HBSS supplemented with 0.1% BSA, 10 mM HEPES and DNase for 1 hr. To obtain a single cell suspension, the dissociated FBr cells were further treated with 0.05% trypsin, 53 mM EDTA (Gibco, Grand Island, N.Y.) for 10–15 min. Debris and aggregates were removed by filtering the cell suspension through a 70-micron filter unit.

Single cell suspensions were obtained after collagenase/hyuronidase treatment followed by trypsinization. Therefore, screening was limited to trypsin-resistant cell surface epitopes.

Bulk cultures of sorted CD45$^+$ or CD34$^+$ cells from FBr failed to initiate neurosphere cultures. Thus, both CD34 and CD45 could be used as negative selectors for human CNS-SC.

To test whether CNS-SC can be isolated based on AC133 expression, human FBr cells were stained with antibodies to CD34, CD45 and AC133. AC133 antigen was defined by two mAbs AC133/1 and AC133/2, both conjugated with phycoerthrin (PE), which are available through Milteny Biotec (Auburn, Calif.). Anti-human CD45-FITC, anti human CD34 conjugated with allophycocyannin (APC) were obtained from CALTAG (Burlingame, Calif.) and BDIS (San Jose, Calif.), respectively. The dissociated FBR cells were incubated with mAbs against CD45-FITC, AC133/1 AC133/2-PE and CD34-APC for 20–60 min on ice. After the final wash, cells were resuspended in HBSS solution containing 0.5 g/mL: propidium iodine (PI). The labeled cells were analyzed and sorted with a dual-laser Vantage SE (BDIS, San Jose). Dead cells were excluded from analysis by their PI staining characteristics. Contaminating blood cells and endothelial cells were excluded by gating out CD45+cells CD34$^+$ cells, respectively. After sorting purity of sorted cell populations were checked.

Figure 9:
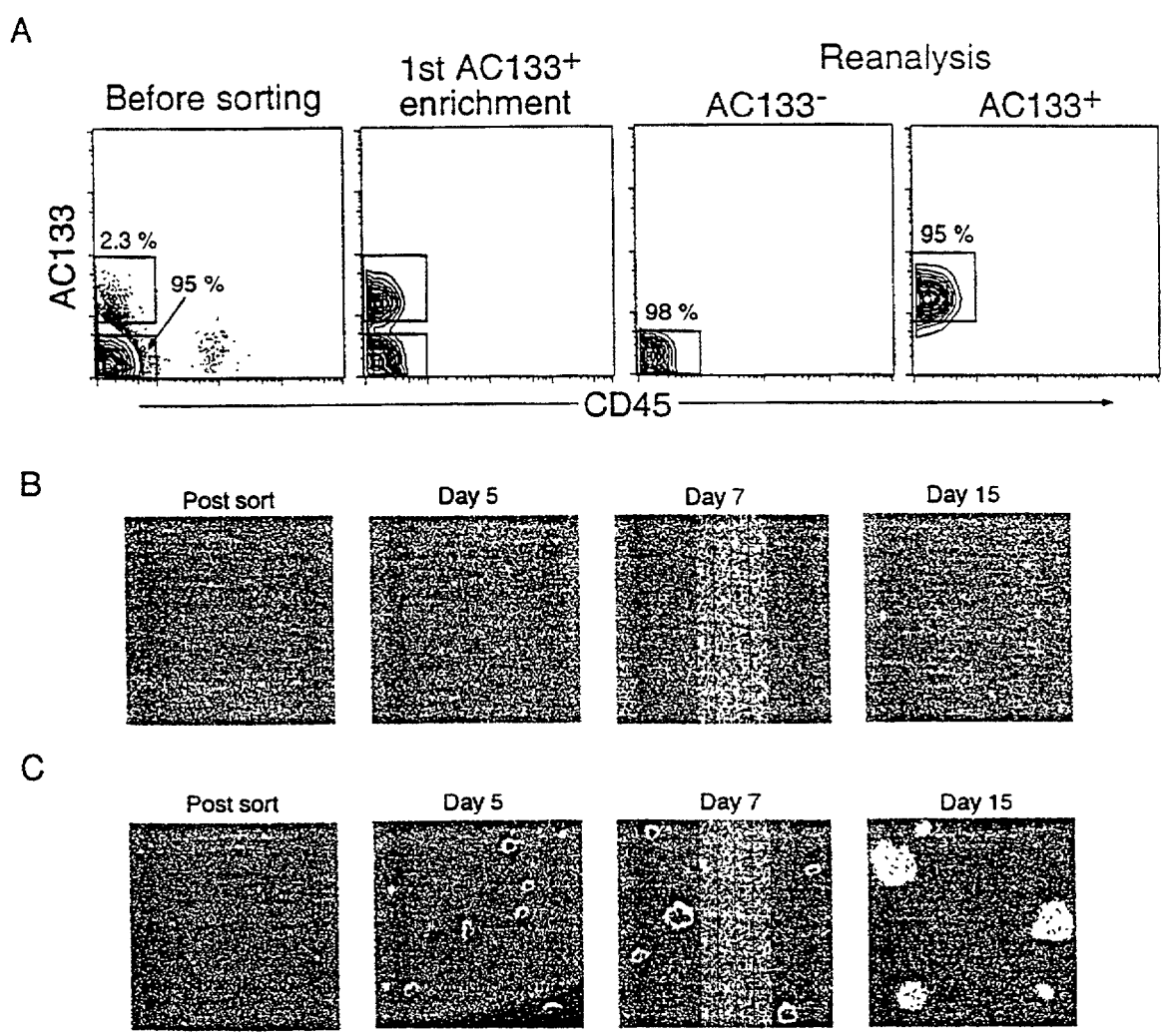
FIG. 9 shows the characteristics of AC133+ cells.

Two cell populations, AC133$^-$CD34$^-$CD45$^-$ (AC133) and AC133$^+$ CD34$^-$CD45$^-$ (AC133$^+$), were sorted and cultured for NS-IC activity. Although AC133 expression appeared initially to be a continuum (FIG. 9A), FACS pre-enrichment of AC133$^+$ cells followed by a second round of cell sorting revealed a distinct AC133$^+$ population (FIG. 9A). In all subsequent tests, both AC133$^-$ and AC133$^+$ subsets were sorted twice, resulting in AC133$^-$ and AC133$^+$ FBr cell fractions with high purity (FIG. 9A).

AC133$^+$ single cell suspensions cultured under neurosphere conditions became blast-like, adhered onto the plastic plate and began to initiate cell division. After 4–5 days in culture, a large fraction of the AC133$^+$ cells began to proliferate and to float as a cluster of a few cells. Small neurospheres were observed as early as 7–10 days after culture initiation (FIG. 9C). In contrast, the sorted AC133⁻ cells remained as a single cell suspension, failed to initiate neurospheres, and eventually died (FIG. 9B). Thus, NS-IC activity is found in the AC133⁺ but not in the AC133-subset of CD45⁻CD34⁻FBr cells.

Only AC133⁺ human FBr cells contain NS-IC activity. Since the qualitative NS-IC assay showed a striking difference in proliferation between AC133⁻ and AC133⁺ subsets, we wanted to determine the frequency of NS-IC in unfractionated (i.e., post cell processed) and various fractionated FBr cell suspensions. Unfractionated FBr cells were plated by limiting dilution (100–10,000 cells/well) into 96-well plates using the FACS automatic cell deposition unit (ACDU). These plates were cultured for 6–8 weeks, and wells that contained neurospheres were scored as positive.

The sorted FBr cells were cultured in neurosphere culture in Ex Vivo 15 (Bio Whittaker, Walkersvile, Md.) media with N2 supplement (Gibco) in the presence of FGF-1 (20 ng/mL), EGF (20 ng/mL), LIF (10 ng/mL), Neural Survival Factor-1 (Clonetics, San Diego, Calif.) and 60 g/mL N-acetyl cystine (Sigma) (Neurosphere-initiation media). The media formulation was optimized based on the frequency analysis of limiting dilution of FBr cells. Cultures were fed weekly and passaged when the neurospheres became large. In some cases, sorted FBr cells were resorted by the automated cell-deposition unit (ACDU) into 96-well plates to evaluate frequency of precursors to initiate neurosphere cultures. These 96-well plates were fed weekly and the presence of neurospheres in wells was scored 6–8 weeks post culture initiation. Linear regression analysis of the proportion of negative wells at each cell concentration was used to determine the frequency of NS-IC.

Multiple neurospheres were detected in the wells plated with high cell doses (i.e., 10,000 cells per well), whereas in the wells plated with a lower cell dose (i.e., 300–1000 cells/well), positive wells contained only single neurospheres. At 100–300 cells per well, only rare wells contained a single neurosphere. When the log of negative wells is plotted versus the number of cells plated per well, a straight line function was found; at 37% negative wells a single hit for NS-IC was determined (FIG. 10A). In a representative tissue shown in FIG. 10A, control processed brain cells contained NS-IC activity at a frequency of 1/880 cells. In the AC 133-subset there was a depletion of NS-IC frequency to 1/4860 cells. In contrast, NS-IC activity was highly enriched in the AC133⁺ subset with a frequency of 1/32 cells (FIG. 10A). NS-IC frequency from 8 different FBr tissues (16–20 gestational weeks) were evaluated as summarized in FIG. 10B and TABLE 5.

TABLE 5

ENRICHMENT OF NS-IC ACTIVITY ISOLATED BY CELL SURFACE MARKERS

| Population | % in brain | NS-IC | NS-IC Range |
|---|---|---|---|
| Brain cell control | 100 | 1/731 | 1/139–1435 |
| AC133⁻ sorted* | 95 | 1/4344 | 1/745–4760 |
| AC133⁺ sorted* | 4.6 | 1/31 | 1/6–1/74 |
| Brain cell control | 100 | 1/1132 | 1/661–1435 |
| 5E12− sorted* | 97 | 1/1335** | 1/1259, 1441 (35672) |
| 5E12+ sorted* | 2.5 | 1/286 | 1/79–392 |

TABLE 5-continued

ENRICHMENT OF NS-IC ACTIVITY ISOLATED BY CELL SURFACE MARKERS

| Population | % in brain | NS-IC | NS-IC Range |
|---|---|---|---|
| Brain cell control | 100 | 1/1030 | 1/399–1435 |
| AC133+ 8G1 $^{-/lo*}$ | 1.1 | 1/23 | 1/15–34 |
| AC133+ 8G1 $^{mid/hi*}$ | 1.7 | 1/63 | 1/38–105 |

*All sorted populations were also gated for CD34⁻ CD45⁻, which represent 98–99% of FBr.
**data excluding one test, as the actual calculated NS-IC frequency indicated in the parentheses. It was due to the most of wells were negative.

In unfractionated fetal brain cells, about 1 in 730 cells contains NS-IC activity. The AC133⁻ subset, representing >95% of FBr contained <1 in 4300 cells with NS-IC and was therefore ~6-fold depleted. In contrast, NS-IC activity was on average enriched 23-fold in the AC133⁺ subset with ~1/31 (range 1/6 to 1/72) fresh FBr cells capable of initiating a neurosphere. Since AC133⁺ cells represent ~4.6% of FBr (i.e., 1 in 22 cells), the enrichment of NS-IC activity virtually paralleled the frequency of AC133⁺ cells in FBr. Thus, AC133⁺ cells contained all detectable NS-IC activity in 16–20 gestational week FBr cell suspensions.

Clonal neurosphere expansion, self-renewal and differentiation from single AC133⁻ sorted cells. To confirm the clonality of neurospheres, single FBr-derived AC133⁺ sorted cells were directly plated into wells of a 96-well plate by the ACDU. After 8 weeks, some wells contained single neurospheres, confirming that these are derived from single AC133⁺ sorted cells (FIG. 10C).

The self-renewal activity of AC133⁺-derived neurospheres was tested for the ability to re-initiate neurosphere cultures. For example, primary neurosphere cultures initiated by AC133⁺-sorted FBr cells were dissociated and re-plated as a single cell per well. Nine 96 wells showed development of a single neurosphere. In one test, neurospheres were clonally derived from AC133⁺-sorted neurosphere cells with about 10% seeding efficiency. Consistently, neurosphere cells which became AC133⁻ failed to re-initiate secondary neurosphere cultures. Thus, these quantitative results demonstrated that NS-IC activity is highly enriched in the AC133⁺ and depleted in the AC133⁻ subset of FBr cells.

To test the differentiation capacity of clonally derived neurosphere cells, single neurospheres were harvested, plated, and induced to differentiate in the presence of the neurotrophic factors, BDNF and GDNF. Neurosphere cells were harvested and disssociated with collagenase and placed onto chamber slides coated with poly-ornithine. They were cultured in the neurosphere-initiation media for one day until they were seeded on the plate. The culture is replaced with differentiation media, consisted from Ex Vivo-15, N2, NAC, BDNF (10 ng/mL), GDNF (10 ng/mL) and laminin (1 g/mL). After 1–2 weeks, chamber slides were fixed with 4% paraformaldehyde in PBS and stained to detect differentiation into neurons and astrocytes, with mAbs against -tubulin and glial fibrillary acidic protein (GFAP).

Under these conditions, the AC133⁺-derived neurospheres differentiated into neurons and astrocytes (FIG. 10D). Together, the data suggest that the mAb AC133 is a marker for NS-IC and can be used to enrich for human CNS-SC. These AC133⁺-derived neurosphere cultures have been continually passaged (>P15 prior to freeze). In a rough estimation, the absolute number of AC133⁺ cells have increased at least 1000 fold by the 5th passage (TABLE 6), and they are capable of re-initiating neurospheres reproducibly. Therefore, AC133 defines a neural cell population that continuously expands and self-renews in vitro.

TABLE 6

EXPANSION OF HUMAN AC133+-SORTED CELLS

| Expansion | Days in cultures | Cell number expansion between Passage 0 to 5 |
| --- | --- | --- |
| Exp. 1 | 87 | 924 |
| Exp. 2 | 76 | 944 |
| Exp. 3 | 96 | 750 |
| Exp. 4 | 74 | 463 |
| Exp. 5 | 110 | 2469 |
| Average | 89 | 1013 |

NS-IC are also enriched in $5E12^+$ and $8G1^{-/lo}$ cells; Generation of novel mAbs. Concurrently with screening the usefulness of available mAbs, we sought to identify novel cell surface markers on human neural cells. FBr cells were dissociated with a combination of collagenase and hyluronidase and were used to immunize BALB/c mice, with a decoy strategy to raise tissue-specific mAbs. About 1900 wells growing hybridoma cells were screened and hybridomas were selected, expanded, and further tested for specific reactivity to human brain. Monoclonal antibodies to human neural cells were produced using a decoy immunization strategy previously described by Yin et al., 90 Blood 5002–12 (1997). Briefly, BALB/c mice were immunized in one footpad with decoy human leucocyte enriched peripheral blood, and in the contralateral footpad with enzyme dissociated human fetal brain cells. The donor lymph node cells draining the human FBr cells immunization were harvested, processed for a cell suspension and fused with a mouse myeloma line. This fusion to a mouse myeloma line has resulted in 1900 wells growing hybridoma cells. Approximately 180 hybridomas were selected, expanded, and further tested for specific reactivity to human brain cells.

As described above, the CNS-SC were highly enriched in the $AC133^-$ subset. To further characterize the phenotype of the CNS-SC, we tested whether $AC133^+$ cells are phenotypically heterogeneous. Thus, $AC133^-$ cells were screened for the co-expression of other markers from the panel of new mAbs. Two novel mAbs, 5E12 and 8G1, were identified. Mab 5E12 co-stains $AC133^+$ cells and long-term neurosphere cells. $5E12^+$ FBr cells are enriched and $5E12^-$ cells are depleted in NS-IC activity (TABLE 5).

Figure 4:
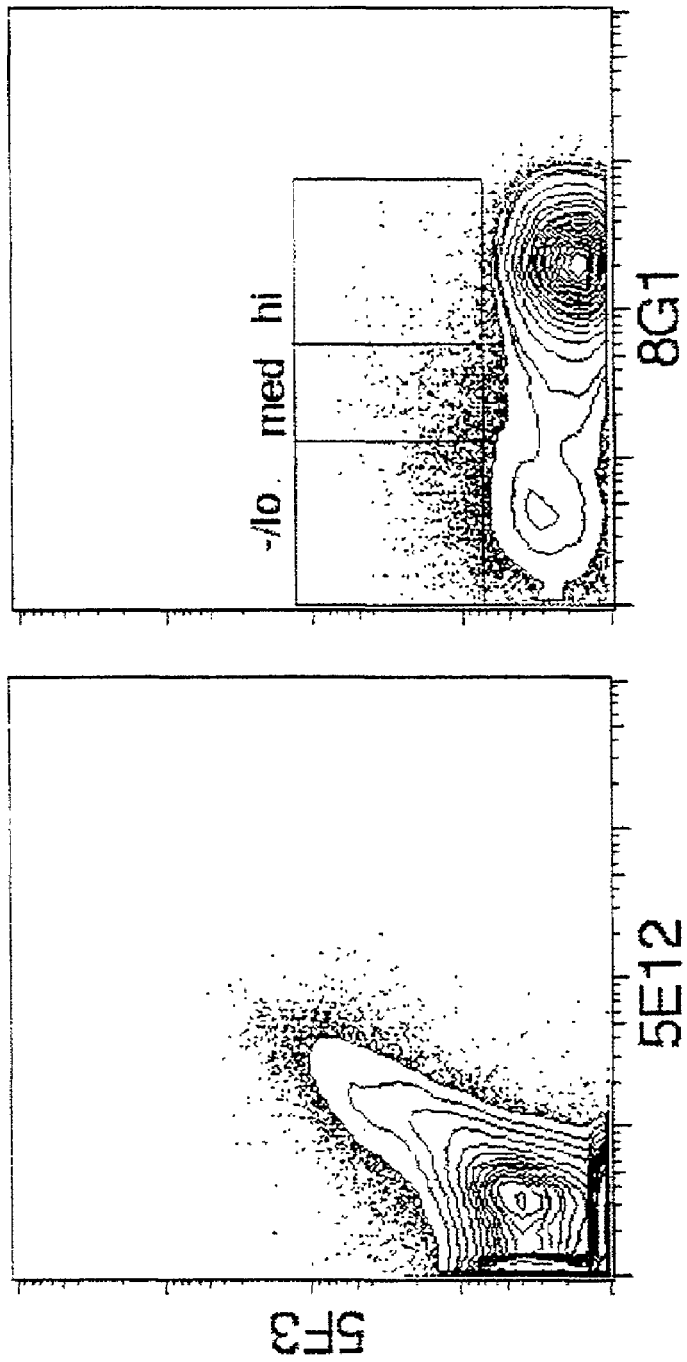
FIG. 4 is a two panel dot plot of FACS sorting data showing the isolation of human neural stem cells by cell surface markers. Human fetal brain cells were enzymatically dissociated as described. Panel A shows that $5F3^+$ cells co-express the antigen for the 5E12 antibody. Panel B shows that $5F3^+$ cells typically do not express the antigen for the 8G1 (CD24) antibody.
Figure 12:
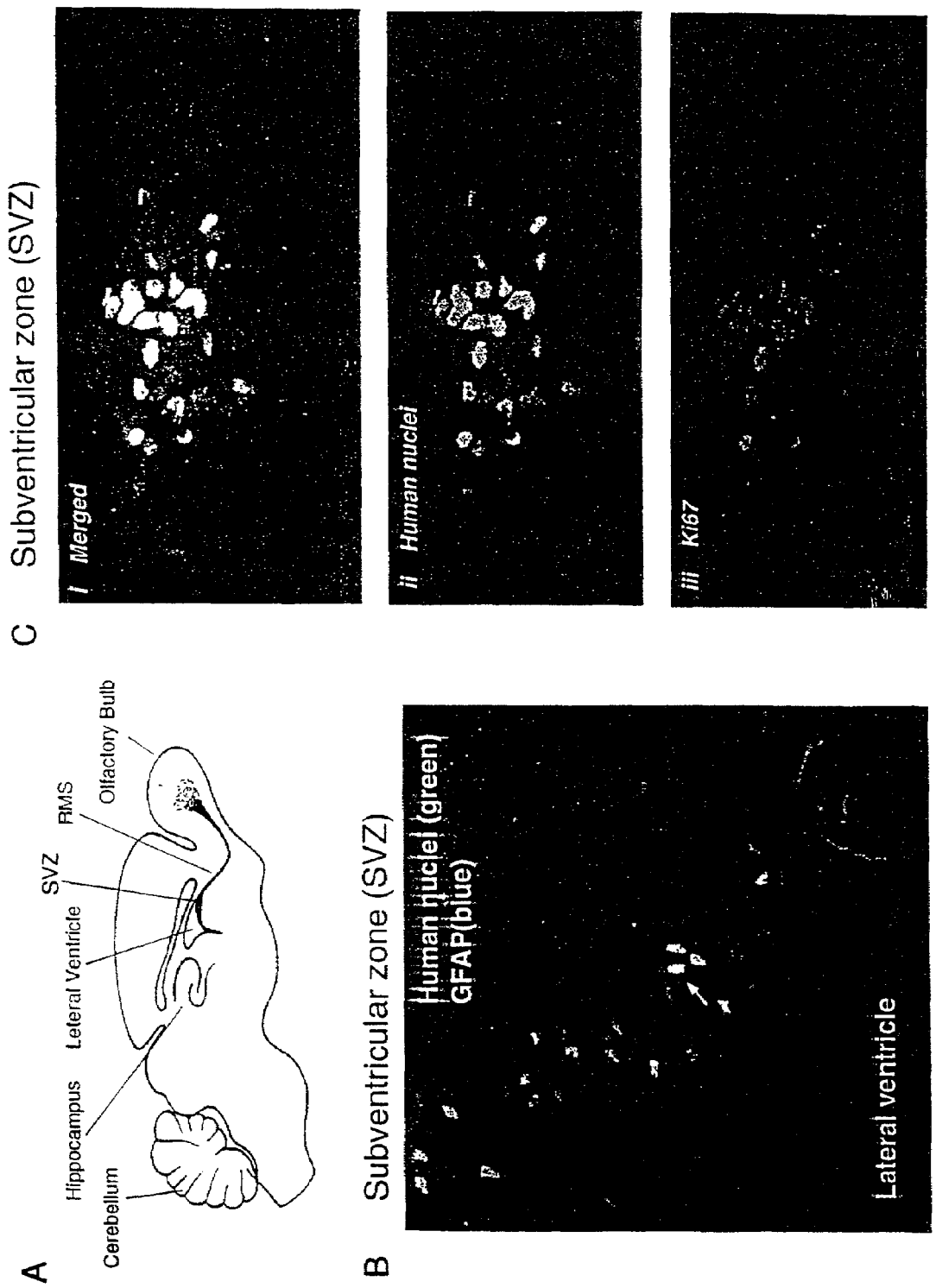
FIG. 12 shows the in vivo long-term proliferation of progeny of transplanted human neurosphere cells in the SVZ of NOD-SCID mice. $AC133^+$-sorted/expanded human neurosphere cells were transplanted into the lateral ventricles of neonatal NOD-SCID mice. Engraftment of human cells were analyzed 7 months after transplantation.

In developing fetal brain, the majority of FBr cells (>90%) expressed a high level of the 8G1 marker (FIG. 4). The $AC133^+$ cells were heterogeneous in 8G1 expression; mostly $8G1^{-/lo}$, some $8G1^{mid}$, and few $8G1^{hi}$ cells (FIG. 12). Interestingly, 8G1 expression on long-term cultured human neurosphere cells was also heterogeneous. Immunoprecipitation and blocking studies determined that 8G1 is an anti-CD24 mAb. Historically, CD24 is known as the heat stable antigen (HSA) and is used widely as a marker in hemato-lymphopoiesis (Alterman et al., 20 Eur J Immunol 1597–602 (1990)). HSA is expressed at low levels on mouse HSCs (Shih & Ogawa, 81 Blood 1155–60 (1993); Spangrude & Scollay, 18 Exp. Hematol. 920–6 (1990)), and at high levels on proB and pre-B cells and thymocytes, and is down regulated completely when these cells become mature lymphocytes (Alterman et al., 20 Eur. J. Immunol. 1597–602 (1990)). As shown in TABLE 5, the frequency of NS-IC is higher in the $AC133^+$ $CD24^{-/lo}$ fraction compared to the $AC133^+CD24^{mid/hi}$ subset.

Potent engraftment ability of $AC133^+$-derived human neurosphere cells. To test the in vivo engraftment, migration and differentiation capacity of human sorted/expanded CNS-SC, $10^5$ or $10^6$ neurosphere cells (initiated from $AC133^+$-sorted FBr cells) were injected into the lateral ventricles of neonatal NOD-SCID mouse brains.

Expanded AC133+ sorted neurosphere cells at passage 6–10 were harvested and gently dissociated with collagenase to obtain small clusters of cells. Cells were resuspended in the equivalent of $0.25\times10^5$ or $2.5\times10^5/L$. Neonatal mice (<24 hrs after birth) were cryo-anesthetized using ice; once anesthetized, the pups were placed on stereotaxic device. A small hole was drilled in the cartilage with a needle and cell suspensions were introduced by Hamiliton syringe into both lateral ventricular spaces. Neonatal mice were injected with 2 1 of cells ranging $10^5$–$10^6$ cells/injection. Pups were revived by warming to monitor the outcome of surgery and then returned to the mother. The injected mice were kept for 7 months prior to testing engraftment of human cells.

Neonatal NOD-SCID mice were chosen as recipients to maximize the participation of injected cells into the neurological system, as cell genesis is still actively in progress in the some parts of neonatal mouse brain. In addition, immunodeficient mice do not reject human tissues, and SCID and NOD-SCID mice have been used as hosts for in vivo studies of human hematopoiesis and tissue engraftment (McCune et al., 241 Science 1632–9 (1988); Kamel-Reid & Dick, 242 Science 1706–9 (1988); Larochelle et al., 2 Nat. Med. 1329–37 (1996)). Seven months after transplantation, animals were sacrificed, and sagittal sections were stained with human specific mAbs against N-CAM and Thy-1 as well as human nuclear antigen.

After 7 months post transplantation, NOD-SCID mice were deeply anesthetized with Avertin and perfused with PBS, followed by 4% paraformaldehycle in phosphate buffer. Brains were post fixed overnight, placed into 30% sucrose solution and frozen in the OCT Compound. Brains were sectioned sagittally at 5 um thickness for futher immunocytochemsitry. To detect human cells in the transplanted mouse brains, sections were stained with mouse monoclonal antibodies against human Thy-1 (Pharmingen, San Diego, Calif.), N-CAM, -tubulin (Sigma) or nuclear antigen (Chemicon) followed by goat anti-mouse IG conjugated with Alexa 488 (Molecular Probe, Eugene, Oreg.)

Staining of these mAbs on mouse brain controls showed no cross-reactivity. Mabs against GFAP and β-tubulin stained both human and mouse cells, and so double labeling with the anti-human nuclei antibody was used to demonstrate human lineage-specific cell populations. Detailed analysis focused particularly on the two sites of the brain previously shown to be sites of active neurogenesis, the subventricular zone (SVZ) of the lateral ventricles and the dentate gyrus of the hippocampus (FIG. 12A).

Human cells were found throughout the mouse brain and were abundant in the SVZ seven months after injection (FIG. 12). For example, in one area many cells with human nuclei+were surrounded by $GFAP^+$ cells (FIG. 12B). Confocal microscopic examinations indicated that most of the human cells were $GFAP^-$, but occasional human $GFAP^+$ cells were also detected (FIG. 12B, arrow).

The transplanted mouse brains were sectioned at 40 micrometer thickness on a microtome and stained with mAbs, and analyzed using a Bio-Rad confocal scanning light microsocope as described previously by Suhonen et al., 383 Nature 624–7 (1996).

Because stem/progenitor cells in the SVZ have been shown to proliferate continuously, we tested whether progeny of the transplanted human AC133$^+$ sorted/expanded neurosphere cells were still proliferating in situ. One section of transplanted brain was stained with Ki67, a marker associated with cell proliferation. Strikingly, a cluster of human cells in the SVZ, nested in GFAP$^+$ cells, co-express Ki-67, indicating that the human cells in SVZ can, like their mouse counterparts, continue to proliferate 7 months post transplantation in the SVZ (FIG. 12C).

Figure 13:
FIG. 13 shows the in vivo migration and differentiation of transplanted human neurosphere cells into the RMS and olfactory bulb. $AC133^+$-sorted/expanded human neurosphere cells were transplanted into lateral ventricle of neonatal NOD-SCID. Engraftment of human cells were analyzed 7 months after transplantation.
Figure 13:
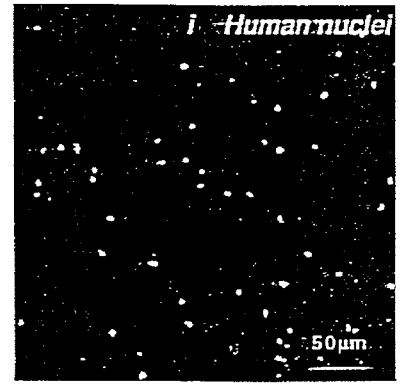
Figure 13:
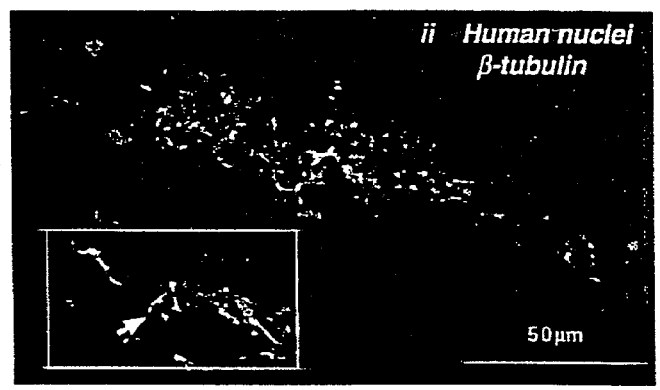
Figure 13:
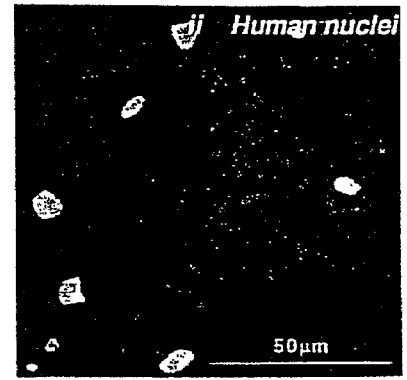
Figure 13:
Figure 13:
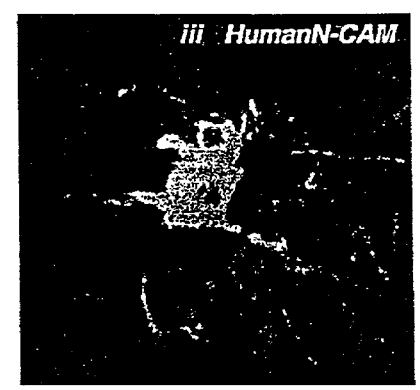

In the olfactory system of rodents, the progeny of stem/progenitor cells that have proliferated in the SVZ enter the rostral migratory stream (RMS) and migrate to the olfactory bulb (Lois & Alvarez-Buylla, 264 Science 1145–8 (1994)). The "chain of neuroblasts" of endogenous rodent progenitors in the RMS express β-tubulin and N-CAM (Fricker et al., 19 J. Neurosci. 5990–6005 (1999); Gage & Cristen, Isolation, characterization and utilization of CNS stem cells (Springer, Heidelberg, 1997)). The sagittal sections containing the RMS were examined for the presence of human neural cells. In mice transplanted with AC133$^+$-sorted neurosphere cells, large numbers of human cells were detected, beginning in the SVZ and extending throughout the RMS (FIG. 13A). Many of these clustered human cells were colocalized with β-tubulin, but it was difficult to identify double positive cells in such clusters. Careful examination of tissues containing fewer human cells revealed multiple cells that were double positive for both β-tubulin and human nuclear antigen (FIG. 13B, arrow). In addition, many of these cells in the RMS expressed the human specific marker, N-CAM (FIG. 13C).

After migrating though the RMS, the progeny of stem/progenitor cells are expected to enter the olfactory bulb and extend toward the olfactory glomerulus to the periglomelular layers of the bulb (Lois & Alvarez-Buylla, 264 Science 1145–8 (1994)). As shown in FIG. 13D, the transplanted progeny of human cells distributed into the glomerular as well as the periglomelular layers. Some of these cells expressed human N-CAM, indicating that they were committed to neuronal lineages. Thus, the progeny of the transplanted sorted/expanded human CNS-SC migrate into the RMS, distribute and differentiate into neuronal lineage in the olfactory bulb. In a few instances tyrosine hydroxylase positive human cells were observed.

Figure 14:
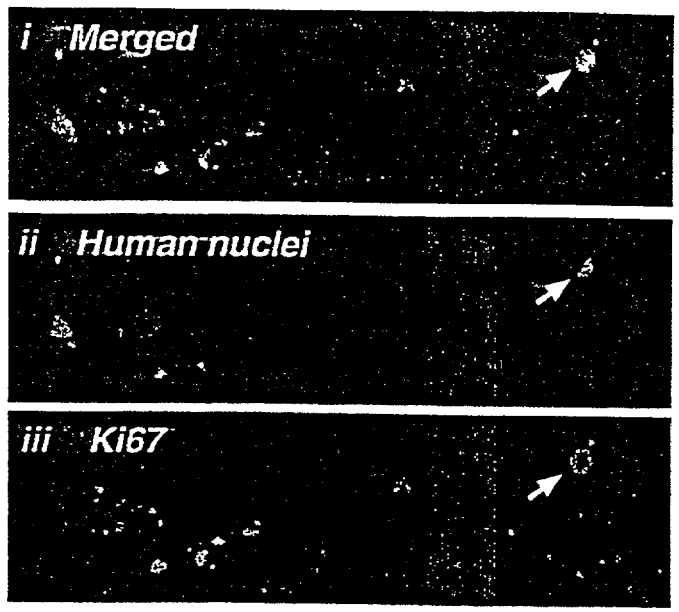
FIG. 14 shows the in vivo long-term proliferation and differentiation of progeny of transplanted human neurosphere cells in the dentate gyrus of hippocampus. $AC133^+$-sorted/expanded human neurosphere cells were transplanted into the lateral ventricle of neonatal NOD-SCID mice. Seven months after transplantation of $AC133^+$-sorted/expanded human neurosphere cells into the lateral ventricles of neonatal NOD-SCID mice proliferating human cells can be found in the hippocampus.
Figure 14:
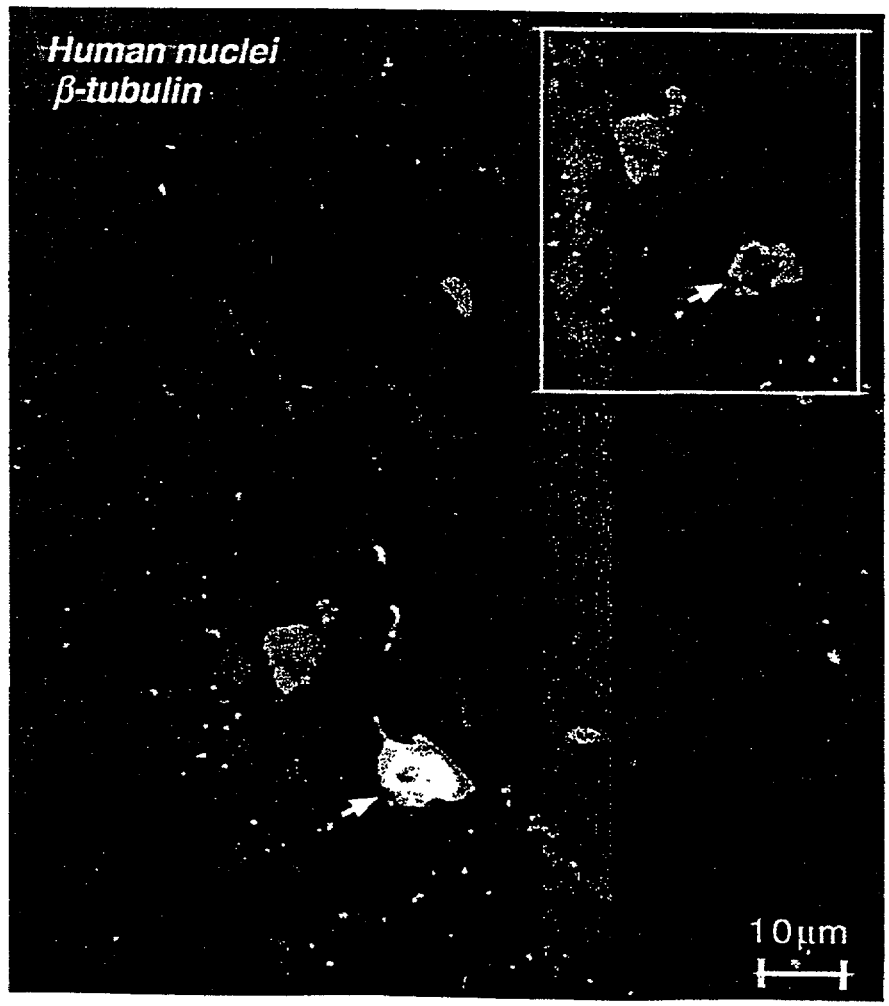

Another site where neurogenesis takes place in adult life is the dentate gyrus of the hippocampus (Gage et al., 92 Proc. Natl. Acad. Sci. USA 11879–83 (1995)). In this EXAMPLE, we found numerous human nuclei cells in the dentate gyrus of the hippocampus. Some of the human cells in the subgranular cell zone co-express Ki-67, indicating that they are still able to proliferate after 7 months post transplantation (FIG. 14A). In a different analysis, some other human cells were β-tubulin$^+$, as expected for developing granular neurons, with their processes extending towards the hilus of the hippocampus (FIG. 14B). These results indicate that not only do these sorted/expanded human CNS-SC engraft, migrate, continue to proliferate, and differentiate, but also their behavior and cell fate were regulated by host cues in a site-specific manner. In no case did the injected cells form tumors.

Discussion. The purpose of this EXAMPLE was to find surface markers on human brain cells that allow the prospective isolation of candidate human CNS-SC. We hypothesized that human neurosphere cultures might be clonally initiated from CNS-SC, and undertook to isolate the NS-IC from fresh human FBr cell suspensions. We demonstrated that 16–20 g.w. human FBr cells contain a rare subset of clonogenic AC133$^+$, 5E12$^+$, 8G1$^{-/lo}$ CD34$^-$CD45$^-$ cells that can initiate neurosphere cultures, self-renew extensively in these cultures, and differentiate in vitro to neurons and glia. Upon transplantation to the lateral ventricles of immunodeficient newborn mice these cells engraft for at least 7 months and give rise to progeny that differentiate, migrate, and some that continued to proliferate (i.e. presence of Ki-67$^+$ human neural cells in the SVZ and dentate gyrus), The engrafted human cells are found in sites wherein their counter-part endogenous mouse neural cells undergo the same events.

Figure 10:
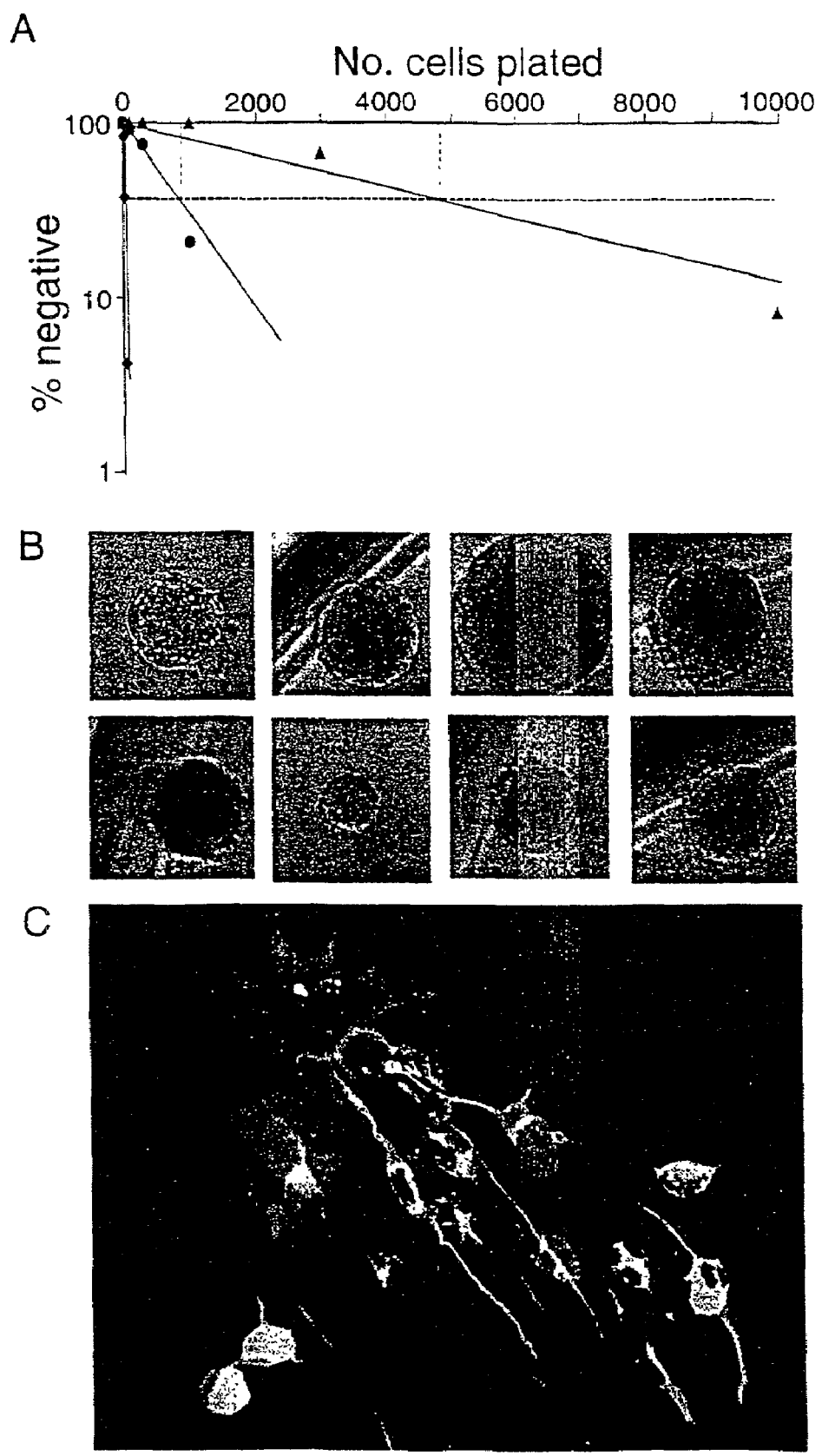
FIG. 10 shows a quantitative analysis of NS-IC activity by limiting dilution and single cell sorting.

The data in FIG. 10 and TABLE 5 demonstrate that there are no other detectable NS-IC cells outside of AC133$^+$ subset in the human fetal brain.

During the analysis of AC133 staining patterns, we noted that ~0.2% of FBr cells express CD34 and remained adherent to cells that were AC133$^+$ CD34$^-$. These CD34$^+$ cells co-expressed the known endothelial cell markers CD105 and CD31 and, after trypsinization, remained as complexes of cells that could inefficiently form some neurospheres when plated at high density in bulk cultures. We have observed similar complexes after a positive selection for CD34-expressing cells. Thus, there is a frequent association of AC133$^+$ CNS-SC and CD34$^-$ endothelial cells that naturally exists. The finding that AC133$^+$ CNS-SC are perivascular, fits with the hypothesis that neurogenesis proceeds pari-passu with angiogenesis.

Figure 11:
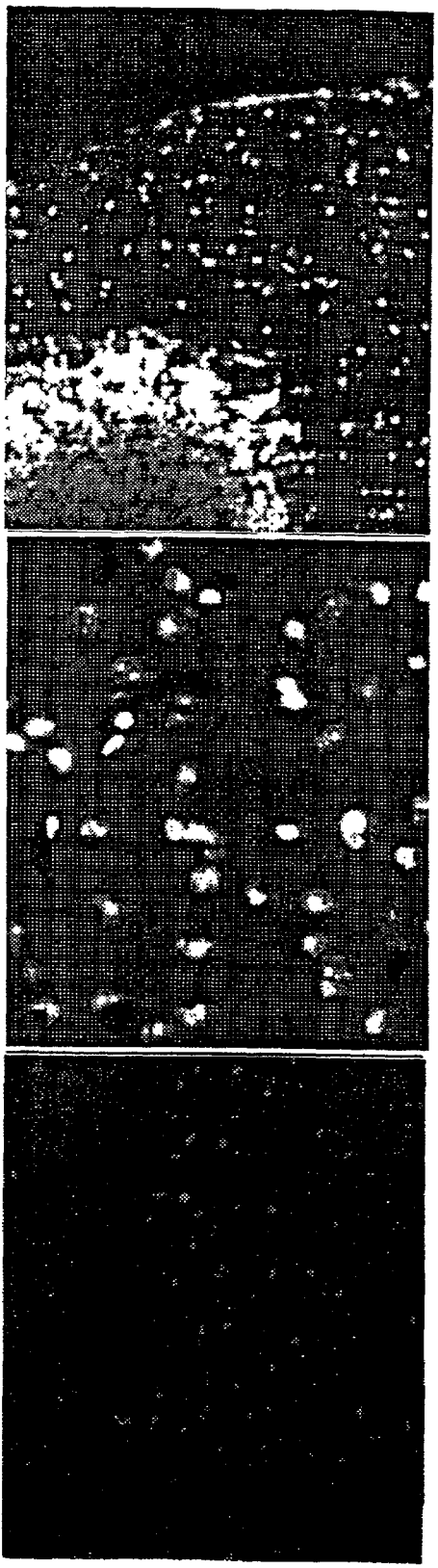
FIG. 11 shows the detection of human neural cells in non-neurogenic sites. In some cases, human neural cells injected into neonatal brain of NOD-SCID mice were detected in corpus callosum, cerebral cortex and cerebellum.

It is striking that the candidate human fetal CNS-SC engraft following injection into the lateral ventricles of neonatal mice and extended throughout the mouse brain. This is a stage of continuing neurogenesis in the mouse, although the extent to which these cells distribute is greater than what one might have expected. In particular, human cells were found adjacent to ventricular spaces, in the hippocampus, in the cerebral cortex, in the corpus callosum, as well as in the cerebellar areas of the brain (FIG. 11). In additions, cells are found both in the SVZ (the area of self-renewal and replication) and along the RMS (the area of differentiation and migration) as well as directly within the olfactory bulb in and near the olfactory glomeruli. Therefore, the injected human CNS-SC are continuing in the processes of neurogenesis at these sites.

Snyder et al. using v-myc immortalized mouse and human neural cell lines, demonstrated this wide ("global") distribution of cells (Yandava et al., 96 Proc Natl Acad Sci USA 7029–34 is (1999)). Here we show that this is a property not only of myc-immortalized cells of murine origin but also of nongenetically modified human CNS-SC.

In contrast to transplantation with teratocarcinoma cells (Trojanowski et al., 122 Exp Neurol 283–94 (1993)), CNS-SC cells do not form neoplastic or hyperplastic aggregates, even when tested 7 months after injection in a fully permissive microenvironment. Therefore CNS-SC cells can reveal developmental and functional pathways inherent in human neuronal systems not modified by the functions of oncogenes or already neoplastically transformed cell lines. The isolation of CNS-SC provides several opportunities for scientific discovery: (i) to delineate directly the lineages that derive from cells at a particular stage or differentiation; (ii) to obtain a gene expression profile of CNS-SC, and their immediate downstream progeny in vitro or in vivo;

(iii) to test whether specific gene modification of the cells allows their engraftment, migration, differentiation, and/or functional integration. The isolation of human CNS stem cells allows for the transplantation of these cells in mouse analogues of human disease, as preclinical tests for their transplantability, differentiation ability, and lack of tumorigenesis.

The foregoing description has been presented only for the purposes of illustration and is not intended to limit the invention to the precise form disclosed, but by the claims appended hereto.

We claim:

1. A method for producing a population highly enriched for human central nervous system stem cells (CNS-SC) which can initiate neurospheres (NS-IC), comprising:
    selecting from a population containing neural or neural-derived cells for cells that bind to a first antibody selected from the group consisting of monoclonal antibody AC133 and monoclonal antibody 5E12, and further comprising the step of further enriching the population by selecting and eliminating from the population those cells that bind to a second antibody selected from the group consisting of a monoclonal antibody that binds to CD45 antigen and a monoclonal antibody that binds to CD34 antigen, such that those cells that are $AC133^+CD45^-$ or $AC133^+CD34^-$ or $5E12^+CD45^-$ or $5E12^+CD34^-$ are selected.

2. The method of claim 1, wherein said first antibody is monoclonal antibody AC133.

3. The method of claim 1, wherein said first antibody is monoclonal antibody 5E12.

4. The method of claim 1, wherein said second antibody is a monoclonal antibody that binds to CD45 antigen.

5. The method of claim 1, wherein said second antibody is monoclonal antibody that binds to CD34 antigen.

6. A method for producing a population highly enriched for human central nervous system stem cells (CNS-SC) which can initiate neurospheres (NS-IC), comprising:
    selecting from a population containing neural or neural-derived cells for cells that bind to monoclonal antibody AC133 and monoclonal 5E12, and further comprising the step of further enriching the population by selecting and eliminating from the population those cells that bind to a monoclonal antibody that binds to CD45 antigen or monoclonal antibody that binds to CD34 antigen, such that those cells that are $AC133^+5E12^+CD45^-$ or $AC133^+5E12^+CD34^-$ are selected.

7. A method for producing a population highly enriched for human central nervous system stem cells (CNS-SC) which can initiate neurospheres (NS-IC), comprising:
    selecting from a population containing neural or neural-derived cells for cells that bind to monoclonal antibody AC133 or monoclonal 5E12, and further comprising the step of further enriching the population by selecting and eliminating from the population those cells that bind to a monoclonal antibody that binds to CD45 antigen and a monoclonal antibody that binds to CD34 antigen, such that those cells that are $AC133^+CD45^-CD34^-$ or $5E12^+CD45^-CD34^-$ are selected.

8. A method for producing a population highly enriched for human central nervous system stem cells (CNS-SC) which can initiate neurospheres (NS-IC), comprising:
    selecting from a population containing neural or neural-derived cells for cells that bind to monoclonal antibody AC133 and to monoclonal antibody 5E12, and further comprising the step of further enriching the population by selecting and eliminating from the population those cells that bind to a monoclonal antibody that binds to CD45 antigen and a monoclonal antibody that binds to CD34 antigen, such that those cells that are $AC133^+5E12^+CD45^-CD34^-$ are selected.

9. The method of any one of claim 1, 6, 7, or 8, further comprising the steps of: further enriching the population by selecting and eliminating from the population those cells that bind to monoclonal antibody 8G1.

10. The method of any one of claim 1, 6, 7, 8, or 9, wherein all of the antibodies are fluorochrome conjugated.

11. The method of any one of claim 1, 6, 7, 8, or 9, wherein all of the antibodies are conjugated to magnetic particles.

12. The method of any one of claim 1, 6, 7, 8, or 9, wherein the selecting is by flow cytometry.

13. The method of any one of claim 1, 6, 7, 8, or 9, wherein the selecting is by fluorescence activated cell sorting or high gradient magnetic selection.

14. The method of any one of claim 1, 6, 7, 8, or 9, wherein the population containing neural or neural-derived cells is obtained from any tissue which gives rise to neural tissue.

15. The method of any one of claim 1, 6, 7, 8, or 9, wherein the population containing neural or neural-derived cells is dissociated from any tissue which gives rise to neural tissue.

16. A method for producing a population enriched for human central nervous system stem cells (CNS-SC) which can initiate neurospheres (NS-IC), comprising selecting from a population of neural or neural-derived cells for cells that bind to monoclonal antibody AC133 or to monoclonal antibody 5E12 or to both monoclonal antibody AC133 and monoclonal antibody 5E12, and further comprising the step of further enriching the population by selecting and eliminating from the population those cells that are $CD45^+$, $CD34^+$, or $CD45^+CD34^+$, wherein the resulting population is enriched for NS-IC as compared to the population of neural or neural-derived cells.

17. The method of claim 16, further comprising the step of further enriching the population by selecting and eliminating from the population those cells that bind to monoclonal antibody 8G1.

18. A method for isolating a neurosphere initiating stem cell (NS-IC), comprising:
    a) combining a population comprising neural cells or neural-derived cells containing a fraction of NS-ICs with monoclonal antibody AC133 or monoclonal antibody 5E12 or both;
    b) selecting the cells that bind to monoclonal antibody AC133 or to monoclonal antibody 5E12 or to both monoclonal antibody AC133 and to monoclonal antibody 5E12, wherein the selected cells are enriched in the fraction of NS-ICs as compared with the population of neural cells;
    c) combining said enriched fraction obtained in step b) with a monoclonal antibody that binds to CD45 antigen or a monoclonal antibody that binds to CD34 antigen or both;
    d) selecting and eliminating $CD45^+$, $CD34^+$, or $CD45^+CD34^+$ cells, wherein the remaining cells are further enriched in the fraction of NS-ICs as compared with the enriched fraction obtained in step b);
    e) introducing at least one cell from the enriched fraction obtained in step d) to a culture medium capable of supporting the growth of NS-IC; and
    f) proliferating the introduced cell in the culture medium.

19. The method of claim 18, wherein the culture medium capable of supporting the growth of NS-IC comprises a growth factor selected from the group consisting of leukocyte inhibitory factor (LIF), epidermal growth factor (EGF), basic fibroblast growth factor (FGF-2) and combinations thereof.

20. The method of claim 18, wherein the culture medium capable of supporting the growth of NS-IC further comprises a neural survival factor, NSF.

21. The method of any one of claim 1, 6, 7, 8, 16, or 18, wherein the population containing neural or neural-derived cells is obtained from a neurosphere culture or an adherent monolayer culture.

* * * * *

UNITED STATES PATENT AND TRADEMARK OFFICE
CERTIFICATE OF CORRECTION

PATENT NO. : 7,037,719 B1  Page 1 of 1
APPLICATION NO. : 09/890469
DATED : May 2, 2006
INVENTOR(S) : David W. Buck, Nobuko Uchida and Irving Weissman It is certified that error appears in the above-identified patent and that said Letters Patent is hereby corrected as shown below:

In claim 6, column 27, line 38, "AC133 and monoclonal 5E12," should read --AC133 and monoclonal antibody 5E12, --

In claim 7, column 27, line 50, "AC133 or monoclonal 5E12," should read --AC133 or monoclonal antibody 5E12, --

In claim 8, column 28, line 2, "$AC133^+5E12^+CD45^{-CD}34^-$" should read -- $AC133^+5E12^+CD45^-CD34^-$ --.

In claim 20, column 29, line 5, "comprises a neural survival factors, NSF." should read -- comprises neural survival facor, NSF."

Signed and Sealed this

Twenty-second Day of August, 2006

JON W. DUDAS
*Director of the United States Patent and Trademark Office*

UNITED STATES PATENT AND TRADEMARK OFFICE
CERTIFICATE OF CORRECTION

PATENT NO.        : 7,037,719 B1
APPLICATION NO. : 09/890469
DATED             : May 2, 2006
INVENTOR(S)       : David W. Buck, Nobuko Uchida and Irving Weissman It is certified that error appears in the above-identified patent and that said Letters Patent is hereby corrected as shown below:

In claim 6, column 27, line 38, "AC133 and monoclonal 5E12," should read --AC133 and monoclonal antibody 5E12, --

In claim 7, column 27, line 50, "AC133 or monoclonal 5E12," should read --AC133 or monoclonal antibody 5E12, --

In claim 8, column 28, line 2, "$AC133^+5E12^+CD45^{-CD}34^-$" should read -- $AC133^+5E12^+CD45^-CD34^-$--.

In claim 20, column 29, line 5, "comprises a neural survival factors, NSF." should read -- comprises neural survival factor, NSF."

This certificate supersedes Certificate of Correction issued August 22, 2006.

Signed and Sealed this

Twenty-fourth Day of October, 2006

JON W. DUDAS
*Director of the United States Patent and Trademark Office*